United States Patent
Winnike et al.

(10) Patent No.: US 12,378,245 B2
(45) Date of Patent: Aug. 5, 2025

(54) CRYSTALLINE FORMS OF AN RSK INHIBITOR

(71) Applicant: PHOENIX MOLECULAR DESIGNS, Vancouver (CA)

(72) Inventors: Richard Winnike, Woodbine, MD (US); Elaine McPherson, Edinburgh (GB); Erik Flahive, San Diego, CA (US); Sandra E. Dunn, Vancouver (CA); Jonathan Loughrey, Edinburgh (GB)

(73) Assignee: PHOENIX MOLECULAR DESIGNS, Vancouver (CA)

( * ) Notice: Subject to any disclaimer, the term of this patent is extended or adjusted under 35 U.S.C. 154(b) by 874 days.

(21) Appl. No.: 17/429,603

(22) PCT Filed: Feb. 10, 2020

(86) PCT No.: PCT/IB2020/000092
§ 371 (c)(1),
(2) Date: Aug. 9, 2021

(87) PCT Pub. No.: WO2020/165646
PCT Pub. Date: Aug. 20, 2020

(65) Prior Publication Data
US 2022/0112193 A1  Apr. 14, 2022

Related U.S. Application Data

(60) Provisional application No. 62/804,076, filed on Feb. 11, 2019.

(51) Int. Cl.
C07D 471/14 (2006.01)
(52) U.S. Cl.
CPC ........ *C07D 471/14* (2013.01); *C07B 2200/13* (2013.01)
(58) Field of Classification Search
CPC .................................................. C07D 471/14
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 5,323,907 | A | 6/1994 | Kalvelage |
| 9,073,926 | B2 | 7/2015 | Boyer et al. |
| 9,150,577 | B2 | 10/2015 | Boyer et al. |
| 9,771,366 | B2 * | 9/2017 | Dunn ............... A61K 45/06 |
| 10,081,632 | B2 * | 9/2018 | Dunn ............... A61K 45/06 |
| 10,758,530 | B2 | 9/2020 | Dunn et al. |
| 2006/0276453 | A1 | 12/2006 | Goldberg et al. |
| 2013/0137680 | A1 | 5/2013 | Boyer et al. |
| 2016/0009726 | A1 | 1/2016 | Vechorkin et al. |
| 2017/0240549 | A1 | 8/2017 | Dunn et al. |
| 2017/0327501 | A1 | 11/2017 | Dunn et al. |
| 2021/0186961 | A1 | 6/2021 | Dunn et al. |

FOREIGN PATENT DOCUMENTS

| | | | |
|---|---|---|---|
| CN | 103724251 | A | 4/2014 |
| EP | 2676137 | B1 | 12/2014 |
| EP | 3416964 | A4 | 9/2019 |
| JP | 2005526831 | A | 9/2005 |
| JP | 2008504291 | A | 2/2008 |
| JP | 2009501126 | A | 1/2009 |
| JP | 2011509238 | A | 3/2011 |
| JP | 2013512952 | A | 4/2013 |
| JP | 2013512953 | A | 4/2013 |
| WO | WO-9815545 | A1 | 4/1998 |
| WO | WO-9820875 | A1 | 5/1998 |
| WO | WO-9850016 | A2 | 11/1998 |
| WO | WO-9900357 | A1 | 1/1999 |
| WO | WO-03087087 | A2 | 10/2003 |
| WO | WO-2005005414 | A2 | 1/2005 |
| WO | WO-2006002421 | A2 | 1/2006 |
| WO | WO-2006108965 | A2 | 10/2006 |
| WO | WO-2008156573 | A1 | 12/2008 |
| WO | WO-2009036175 | A2 | 3/2009 |
| WO | WO-2009040512 | A2 | 4/2009 |
| WO | WO-2011071716 | A1 | 6/2011 |
| WO | WO-2011071725 | A1 | 6/2011 |
| WO | WO-2013181742 | A1 | 12/2013 |
| WO | WO-2015155042 | A1 | 10/2015 |
| WO | WO-2017141116 | A1 * | 8/2017 ........... A61K 31/337 |
| WO | WO-2020165646 | | 8/2020 |

OTHER PUBLICATIONS

Australian Application No. 2017220738 First Examination Report dated Mar. 11, 2021.
Bernstein: Crystal Structure Prediction and Polymorphism. ACA Transactions 39:14-23 (2004).
Burger's medicinal chemistry and drug discovery. Fifth Edition. vol. 1: Principles and Practice, New York: John Wiley & Sons, edited by Manfred E. Wolff. 4 pp. 975-977, 1994.

(Continued)

*Primary Examiner* — John S Kenyon
*Assistant Examiner* — Rehana Ismail
(74) *Attorney, Agent, or Firm* — Wilson Sonsini Goodrich & Rosati

(57) ABSTRACT

Described herein are crystalline forms of (R)-N-(1-(4-aminobenzyl)-1H-pyrazol-4-yl)-9-methyl-6-oxo-6,7,8,9-tetrahydropyrido [3',2': 4,5]-pyrrolo [1,2-a]pyrazine-2-carboxamide hydrochloride and solvates thereof; pharmaceutical compositions and use thereof in treating cancer such as breast cancer, prostate cancer, lung cancer, brain cancer, skin cancer, bone cancer, ovarian cancer, multiple myeloma and leukemia. Compound (I).

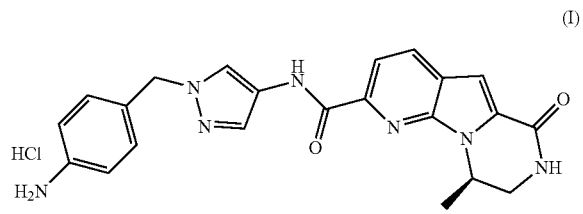

(I)

15 Claims, 7 Drawing Sheets

(56) References Cited

OTHER PUBLICATIONS

CAS Registry No. 1789841-92-4 (2021).
CAS Registry No. 1790418-43-7 (2021).
CAS Registry No. 1790836-52-0 (2021).
Castellana et al.: Interplay between YB-1 and IL-6 promotes the metastatic phenotype in breast cancer cells. Oncotarget 6(35):38239-38256, 2015.
Clark et al.: The serine/threonine protein kinase, p90 ribosomal S6 kinase, is an important regulator of prostate cancer cell proliferation. Cancer Res 65(8):3108-3116, 2005.
Columbian Application No. NC2018/0008846 Office Action Resolution No. 30527 dated May 20, 2021.
Columbian Application No. NC2018/0008846 Office Action Resolution No. 71319 dated Nov. 9, 2020.
Davies et al.: Inhibition of RSK with the novel small-molecule inhibitor LJI308 overcomes chemoresistance by eliminating cancer stem cells. Oncotarget 6(24):20570-20577, 2015.
Davies et al.: YB-1 transforms human mammary epithelial cells through chromatin remodeling leading to the development of basal-like breast cancer. Stem Cells 32(6):1437-1450, 2014.
Dhillon et al.: The expression of activated Y-box binding protein-1 serine 102 mediates trastuzumab resistance in breast cancer cells by increasing CD44+ cells. Oncogene 29:6294-6300, 2010.
Dorwald, F.Zaragoza. Side reactions in organic synthesis: A guide to successful synthesis design. Wiley-VCH Verlag GmbH & Co., Weinham, Preface, 6 pages, 2005.
European Patent Application No. EP17752742.1 Office Action dated Oct. 4, 2019.
European Patent Application No. EP17752742.1 Search Report dated Aug. 16, 2019.
Fryer et al.: Mitigation of off-target adrenergic binding and effects on cardiovascular function in the discovery of novel ribosomal S6 kinase 2 inhibitors. Journal of Pharmacology and Experimental Therapeutics, 340(2):492-500, 2012.
Gluz et al.: Triple-negative breast cancer—current status and future directions. Annals of Oncology, 20(12):1913-1927.
Hackam et al.: Translation of research evidence from animals to humans. JAMA, 296(14):1731-1732, 2006.
Imada et al.: Mutual regulation between Raf/MEK/ERK signaling and Y-box-binding protein-1 promotes prostate cancer progression. Clin Cancer Res 19(17):4638-4650, 2013.
Japanese Application No. 2018-543101 Reason for Refusal dated Feb. 1, 2021.
Jones et al.: Pharmaceutical Cocrystals: An Emerging Approach to Physical Property Enhancement. MRS Bulletin 31:875-879 (2006).
Jordan, V.Craig. Tamoxifen: A Most unlikely pioneering medicine. Nature Reviews: Drug Discovery, 2:205-213, 2003.
Kang, S., and J. Chen. Targeting RSK2 in human malignancies. Expert Opin Ther Targets 15(1):11-20, 2011.
Kuzma et al.: Regional Anesthesia 22(6):543-551, 1997 (Abstract only).
Larrea et al.: RSK1 drives p27Kip1 phosphorylation at T198 to promote RhoA inhibition and increase cell motility. Proc Natl Acad Sci USA 106(23):9268-9273, 2009.
Li et al.: The prometastatic ribosomal S6 kinase 2-cAMP response element-binding protein (RSK2-CREB) signaling pathway up-regulates the actin-binding protein fascin-1 to promote tumor metastasis. J Biol Chem 288:32528-32538, 2013.
Ma et al.: Ribosomal protein S6 kinase (RSK)-2 as a central effector molecule in RON receptor tyrosine kinase mediated epithelial to mesenchymal transition induced by macrophage-stimulating protein. Mol Cancer 28(10):1-15, 2011.
Mexican Patent Application No. MX/a/2018/010028 Office Action dated Feb. 28, 2020.
Pambid et al.: Overcoming resistance to Sonic Hedgehog inhibition by targeting p90 ribosomal S6 kinase in pediatric medulloblastoma. Pediatr Blood Cancer 61(1):107-115, 2014.
Panupinthu et al.: Self-reinforcing loop of amphiregulin and Y-box binding protein-1 contributes to poor outcomes in ovarian cancer. Oncogene 33(22):2846-2856, 2014.
PCT/IB2017/000237 International Search Report and Written Opinion dated Jul. 7, 2017.
PCT/IB2020/000092 International Preliminary Report on Patentability dated Aug. 26, 2021.
PCT/IB2020/000092 International Search Report and Written Opinion dated Jun. 23, 2020.
Peng et al.: Tumor necrosis factor receptor-associated factor family protein 2 is a key mediator of the epidermal growth factor-induced ribosomal S6 kinase 2/cAMP-responsive element-binding protein/Fos protein signaling pathway. J Biol Chem 287(31):25881-25892, 2012.
Poomakkoth et al.: p90 ribosomal S6 kinase: a potential therapeutic target in lung cancer. J Transl Med 14:1-6, 2016.
Price. The computational prediction of pharmaceutical crystal structures and polymorphism. Advanced Drug Delivery Reviews 56:301-319 (2004).
Reipas et al.: Luteolin is a novel p90 ribosomal S6 kinase (RSK) inhibitor that suppresses Notch4 signaling by blocking the activation of Y-box binding protein-1 (YB-1), Oncotarget 4(2):329-345, 2013.
Rico-Bautista et al.: Chemical genetics approach to restoring p27Kip1 reveals novel compounds with antiproliferative activity in prostate cancer cells. BMC Biology. 8:153 (2010).
Romeo et al.: Regulation and function of the RSK family of protein kinases. Biochem J 441(2):553-569, 2012.
Salhi et al.: RSK1 activation promotes invasion in nodular melanoma. Am J Pathol 185(3): 704-716, 2015.
Shahbazian et al.: The mTOR/PI3K and MAPK pathways converge on eIF4B to control its phosphorylation and activity. EMBO Journal, 25(12): 2781-2791.
Shiota et al.: Interaction between docetaxel resistance and castration resistance in prostate cancer: implications of Twist1, YB-1, and androgen receptor. Prostate 73(12):1336-1344, 2013.
Shiota et al.: Potential Role for YB-1 in Castration-Resistant Prostate Cancer and Resistance to Enzalutamide Through the Androgen Receptor V7. J Natl Cancer Inst 108(7):djw005, 10 pages. (ahead of print), 2016.
Smith et al.: Identification of the first specific inhibitor of p90 ribosomal S6 kinase (RSK) reveals an unexpected role for RSK in cancer cell proliferation. Cancer Res 65(3):1027-1034, 2015.
Stratford et al.: Epidermal growth factor receptor (EGFR) is transcriptionally induced by the Y-box binding protein-1 (YB-1) and can be inhibited with Iressa in basal-like breast cancer, providing a potential target for therapy. Breast Cancer Res 9:R61, 2007.
Stratford et al.: Targeting p90 ribosomal S6 kinase eliminates tumor-initiating cells by inactivating Y-box binding protein-1 in triple-negative breast cancers. Stem Cells 30(7):1338-1348, 2012.
Stratford et al.: The promise and challenges of targeting RSK for the treatment of cancer. Expert Opin Ther Targets 15(1):1-4, 2011.
Stratford et al.: Y-box binding protein-1 (YB-1) serine 102 is a downstream target of p90 ribosomal S6 kinase (RSK) in basal-like breast cancer cells. Breast Cancer Res 10(6):R99:Epub ahead of print, 2008.
U.S. Appl. No. 15/665,181 Notice of Allowance Mailed Aug. 20, 2018.
U.S. Appl. No. 15/436,587 Notice of Allowance dated Oct. 5, 2017.
U.S. Appl. No. 15/436,587 Office Action dated Apr. 25, 2017.
U.S. Appl. No. 15/665,181 Office Action dated Feb. 9, 2018.
U.S. Appl. No. 16/077,029 Notice of Allowance dated Jul. 2, 2020.
U.S. Appl. No. 16/077,029 Office Action dated Sep. 9, 2019.
Vippagunta et al.: Crystalline solids. Advanced Drug Delivery Reviews, 48:3-26, 2001.
Vogel et al.: Efficacy and safety of trastuzumab as a single agent in first-line treatment of Her-2 over-expressing metastatic breast cancer. J Clin Onc 20:719-726, 2002.
Ward, Chiral separations. Analytical Chemistry, 74(12)2863-2872, 2002.
Xiong et al.: Synthesis and SAR studies of indole-based MK2 inhibitors. Bioorganic and Medicinal Chemistry Letters, 18:1994-1998, 2008.

(56) References Cited

OTHER PUBLICATIONS

Yoo et al.: The conformation and activity relationship of benzofuran derivatives as angiotensin II receptors antagonists. Bioorg. & Med. Chem., 5(2):445-459, 1997.

Zhang et al.: Myricetin exerts anti-proliferative, anti-invasive, and pro-apoptotic effects on esophageal carcinoma EC9706 and KYSE30 cells via RSK2. Tumour Biol 35(12):12583-12592, 2014.

Zhu et al.: RNA interference screening identifies lenalidomide sensitizers in multiple myeloma, including RSK2. Blood 125:483-491, 2015.

Augsburger, Larry L., et al. Pharmaceutical Dosage Forms: Tablets. Informa Healthcare, 3rd Edition, 2:62-66 (2008).

Brittain, H.G., et al. Polymorphism in Pharmaceutical Solids. Marcel Dekker, Inc., vol. 192, 1-10; 183-226 (1999).

Byrn, Stephen, et al. Pharmaceutical Solids: A Strategic Approach to Regulatory Considerations. Pharmaceutical Research, vol. 12, 945-954 (1995).

Caira, Mino R. Crystalline Polymorphism of Organic Compounds. In: Design of Organic Solids, Topics in Current Chemistry. Springer 198:163-208 (1998).

EP20756543.3 Extended European Search Report dated Oct. 17, 2022.

Handbook of organic compound crystal preparation. Maruzen Co., Ltd.), Edited by Noriaki Hirayama. pp. 17-23, 37-40, 45-51, 57-65 (2008).

JP2021-546803 Office Action dated Jan. 22, 2024, and an English translation.

Kawaguchi, et al. Drug and crystal polymorphism. Journal Human environment engineering 4(2): 310-317 (2002).

Unknown. The polymorphism of medicines and crystallisation of medicines. pp. 273, 278, 305-17 (2002).

U.S. Appl. No. 16/917,595 Notice of Allowance dated Aug. 2, 2023.
U.S. Appl. No. 16/917,595 Office Action dated Jan. 6, 2023.
U.S. Appl. No. 16/917,595 Office Action dated May 11, 2022.

* cited by examiner

CRYSTALLINE FORMS OF AN RSK INHIBITOR

CROSS-REFERENCE

This application is a National Stage Entry of PCT/IB2020/000092, filed on Feb. 10, 2020, which claims the benefit of U.S. Provisional Application No. 62/804,076, filed on Feb. 11, 2019, all of which are hereby incorporated in their entireties.

BACKGROUND

The p90 ribosomal S6 kinase (RSK) family is comprised of four isoforms, RSK1, RSK2, RSK3 and RSK4. These isoforms are pivotal for transmitting cell signalling from cell surface receptors such as growth factors, hormones, and cytokines. RSK1 and RSK2 are the isoforms most common to cancer where they control cell growth, invasion and the suppression of apoptosis. RSK3 is not commonly expressed in cancer, however, it has been associated with drug resistance as have RSK1 and RSK2. RSK4 is not commonly expressed in cancer. The RSK family is also fundamental to inflammation, diabetes, and heart disease.

In the field of oncology, RSK inhibitors provide an opportunity for targeted therapy to improve the treatment of cancer. Inhibiting RSK also affords an opportunity to overcome drug resistance through multiple mechanisms including the elimination of cancer stem cells (CSC) or tumor-initiating cells (TIC). RSK inhibitors can reportedly overcome resistance to targeted therapies such as Herceptin, Gefitinib, and Enzalutamide. RSK inhibitors can also be used to augment resistance to microtubule cytotoxics such as paclitaxel.

There are many types of cancers associated with RSK activity, including, but not limited to, breast, prostate, lung, brain, blood, skin, bone, and ovarian cancers. In the field of breast and prostate cancer research, RSK inhibitors have been shown to block hormone signalling. As with many types of cancer, those that arise in the breast are genetically diverse and as such have been categorized into three main types: Type 1, which is hormone positive expressing the estrogen and progesterone receptors (ER and PR respectively); Type 2, which is Her-2 positive; and Type 3, which is triple-negative as the cancer cells lack ER, PR and Her-2 receptors. The triple-negative breast cancer (TNBC) is currently considered the most aggressive and is associated with the worst outcomes for patients. It constitutes 15-25% of all breast cancers and is more common in younger women. Women with mutations in the breast cancer susceptibility genes 1 and 2 (BRCA1 and BRCA2) are more likely to develop TNBC then the other types of breast cancer.

Accordingly, there is a need for small molecule inhibitors of RSK which are useful in treating diseases and conditions associated with the activity of RSK, such as cancer.

SUMMARY OF THE INVENTION (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride is an RSK inhibitor. In one aspect, described herein is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof.

In one embodiment, is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride is Form 1 having at least one of the following properties:
  (a) an X-ray powder diffraction (XRPD) pattern substantially the same as shown in FIG. 1;
  (b) an X-ray powder diffraction (XRPD) pattern with characteristic peaks at 9.6° 2-Theta, 16.2° 2-Theta, 18.2° 2-Theta, 21.2° 2-Theta, 22.0° 2-Theta, and 24.8° 2-Theta;
  (c) a thermo-gravimetric analysis (TGA) substantially similar to the one set forth in FIG. 2;
  (d) a DSC thermogram substantially similar to the one set forth in FIG. 3;
  (e) a DSC thermogram with an endotherm having an onset at about 171° C.;
  (f) monohydrate; or
  (g) combinations thereof.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has an X-ray powder diffraction (XRPD) pattern substantially the same as shown in FIG. 1.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has an X-ray powder diffraction (XRPD) pattern with characteristic peaks at 9.6° 2-Theta, 16.2° 2-Theta, 18.2° 2-Theta, 21.2° 2-Theta, 22.0° 2-Theta, and 24.8° 2-Theta.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has a thermogravimetric analysis (TGA) substantially similar to the one set forth in FIG. 2.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has a DSC thermogram substantially similar to the one set forth in FIG. 3.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has a DSC thermogram with an endotherm having an onset at about 171° C.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form is a monohydrate.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form is characterized as having properties: (a) an X-ray powder diffraction (XRPD) pattern substantially the same as shown in FIG. 1; (b) an X-ray powder diffraction (XRPD) pattern with characteristic peaks at 9.6° 2-Theta, 16.2° 2-Theta, 18.2° 2-Theta, 21.2° 2-Theta, 22.0° 2-Theta, and 24.8° 2-Theta; (c) a thermogravimetric analysis (TGA)

substantially similar to the one set forth in FIG. 2; (d) a DSC thermogram substantially similar to the one set forth in FIG. 3; (e) a DSC thermogram with an endotherm having an onset at about 171° C.; and (f) monohydrate.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form is obtained from methanol/water or alcohol/water.

In another embodiment, is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride is Form 2 having at least one of the following properties:

(a) an X-ray powder diffraction (XRPD) pattern substantially the same as shown in FIG. 4;
(b) an X-ray powder diffraction (XRPD) pattern with characteristic peaks at 10.4° 2-Theta, 15.1° 2-Theta, 18.0° 2-Theta, 19.5° 2-Theta, 25.4° 2-Theta, and 26.8° 2-Theta;
(c) a thermogravimetric analysis (TGA) substantially similar to the one set forth in FIG. 5;
(d) a DSC thermogram substantially similar to the one set forth in FIG. 6;
(e) a DSC thermogram with an endotherm having an onset at about 230° C.; or
(f) combinations thereof.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has an X-ray powder diffraction (XRPD) pattern substantially the same as shown in FIG. 4.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has an X-ray powder diffraction (XRPD) pattern with characteristic peaks at 10.4° 2-Theta, 15.1° 2-Theta, 18.0° 2-Theta, 19.5° 2-Theta, 25.4° 2-Theta, and 26.8° 2-Theta.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has a thermogravimetric analysis (TGA) substantially similar to the one set forth in FIG. 5.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has a DSC thermogram substantially similar to the one set forth in FIG. 6.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form has a DSC thermogram with an endotherm having an onset at about 230° C.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form is characterized as having properties: (a) an X-ray powder diffraction (XRPD) pattern substantially the same as shown in FIG. 4; (b) an X-ray powder diffraction (XRPD) pattern with characteristic peaks at 10.4° 2-Theta, 15.1° 2-Theta, 18.0° 2-Theta, 19.5° 2-Theta, 25.4° 2-Theta, and 26.8° 2-Theta; (c) a thermogravimetric analysis (TGA) substantially similar to the one set forth in FIG. 5; (d) a DSC thermogram substantially similar to the one set forth in FIG. 6; and (e) a DSC thermogram with an endotherm having an onset at about 230° C.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, wherein the crystalline form is obtained from acetonitrile, methanol, ethanol, methyl ethyl ketone, 1,4-dioxane, 1-propanol, 2-propanol, or dimethylformamide.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, wherein the crystalline form is unsolvated.

In some embodiments is a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, for use in medicine.

In some embodiments is (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, wherein (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride is amorphous.

In another aspect, described herein is a pharmaceutical composition comprising a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, or solvate thereof, and at least one inactive ingredient selected from pharmaceutically acceptable carriers, diluents, and excipients.

In another aspect is a method of treating a disease or condition associated with RSK activity in a mammal, wherein the method comprises administering to the mammal a therapeutically effective amount of a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride described herein, or a solvate thereof. In some embodiments, the disease or condition associated with RSK activity in a mammal is cancer. In some embodiments, the cancer is breast cancer, prostate cancer, lung cancer, brain cancer, skin cancer, bone cancer, ovarian cancer, multiple myeloma or leukemia. In some embodiments is a method of treating a disease or condition associated with RSK activity in a mammal, wherein the method comprises administering to the mammal a therapeutically effective amount of a crystalline form of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride described herein, or a solvate thereof; further comprising the administration of a second therapeutic agent. In some embodiments, the second therapeutic agent is a chemotherapeutic agent, hormonal therapeutic agent, or an immunotherapeutic agent. In some embodiments, the second therapeutic agent is a poly ADP-ribose polymerase (PARP) inhibitor, STAT 3 inhibitor, Janus Kinase inhibitor, or EGFR inhibitor. In some embodiments, the second therapeutic agent is a chemotherapeutic agent (small molecule or antibody). In some embodiments, the second therapeutic agent is paclitaxel. In some embodiments, the second therapeutic agent is methotrexate. In some embodiments, the second therapeutic agent is 5-fluorouracil. In some embodiments, the second therapeutic agent is adriamycin.

In some embodiments, the method further comprises the administration of radiation therapy.

INCORPORATION BY REFERENCE

All publications, patents, and patent applications mentioned in this specification are herein incorporated by reference to the extent applicable and relevant and to the same extent as if each individual publication, patent, or patent application was specifically and individually indicated to be incorporated by reference.

Figure 1:
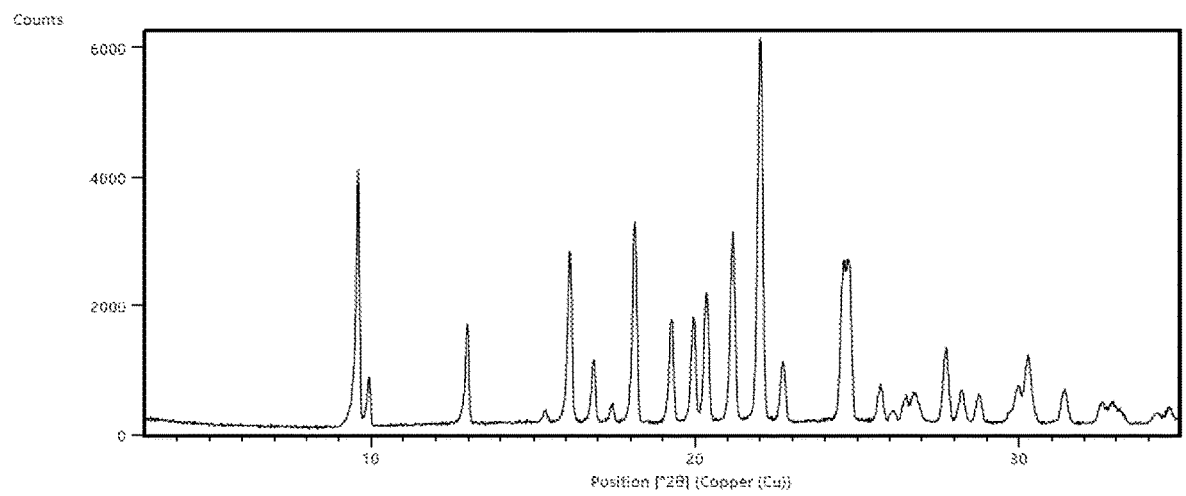
FIG. 1. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 1.

DETAILED DESCRIPTION OF THE INVENTION (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride is an RSK inhibitor. Described herein are crystalline forms of (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide dihydrochloride (Compound 2), and (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide free base (Compound 3).

Compound 1

In one embodiment is (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1). "Compound 1" or "(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride" refers to the compound with the following structure:

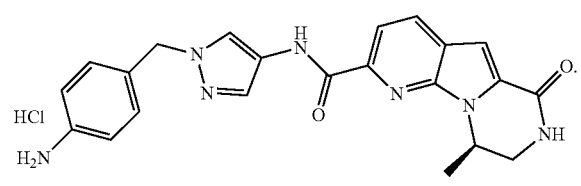 [SMILES: Cl ; C[C@@H]1CNC(=O)c2cc3ccc(C(=O)Nc4cnn(Cc5ccc(N)cc5)c4)nc3n21]

Compound 2

In another embodiment is (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide dihydrochloride (Compound 2). "Compound 2" or "(R)—N-(1-(4-aminobenzyl)-1H-pyrazol-4-yl)-9-methyl-6-oxo-6,7,8,9- tetrahydropyrido[3',2':4,5]pyrrolo[1,2-a]pyrazine-2-carboxamide dihydrochloride" refers to the compound with the following structure:

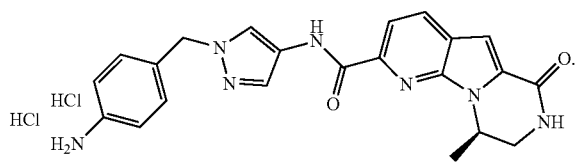 [SMILES: Cl ; Cl ; C[C@@H]1CNC(=O)c2cc3ccc(C(=O)Nc4cnn(Cc5ccc(N)cc5)c4)nc3n21]

Compound 3

In another embodiment is (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide free base (Compound 3). "Compound 3" or "(R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide free base" refers to the compound with the following structure:

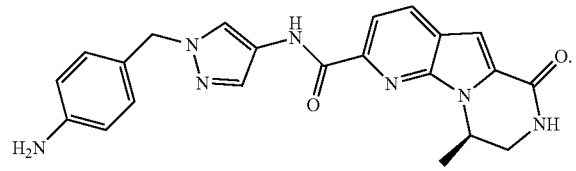 [SMILES: C[C@@H]1CNC(=O)c2cc3ccc(C(=O)Nc4cnn(Cc5ccc(N)cc5)c4)nc3n21]

In some embodiments, Compound 1 includes the solvent addition forms (solvates). In some embodiments, Compound 2 includes the solvent addition forms (solvates). In some embodiments, Compound 3 includes the solvent addition forms (solvates).

Solvates contain either stoichiometric or non-stoichiometric amounts of a solvent, and are formed during the process of product formation or isolation with pharmaceutically acceptable solvents such as water, ethanol, methanol, tert-butyl methyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In some embodiments, solvates are formed using, but not limited to, Class 3 solvent(s). In some embodiments, solvates are formed using, but not limited to, Class 2 solvent(s). Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016). Hydrates are formed when the solvent is water, or alcoholates are formed when the solvent is alcohol.

In other embodiments, Compound 1 is prepared in various forms, including but not limited to, an amorphous phase, crystalline forms, milled forms, and nano-particulate forms. In other embodiments, Compound 2 is prepared in various forms, including but not limited to, an amorphous phase, crystalline forms, milled forms, and nano-particulate forms. In other embodiments, Compound 3 is prepared in various forms, including but not limited to, an amorphous phase, crystalline forms, milled forms, and nano-particulate forms.

While not intending to be bound by any particular theory, certain solid forms are characterized by physical properties, e.g., stability, solubility, and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein.

Crystalline Forms

The identification and selection of a solid form of a pharmaceutical compound are complex, given that a change in solid form may affect a variety of physical and chemical properties, which may provide benefits or drawbacks in processing, formulation, stability, bioavailability, storage, and handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable, and marketable pharmaceutical product.

Crystalline Compound 1, Form 1

Figure 2:
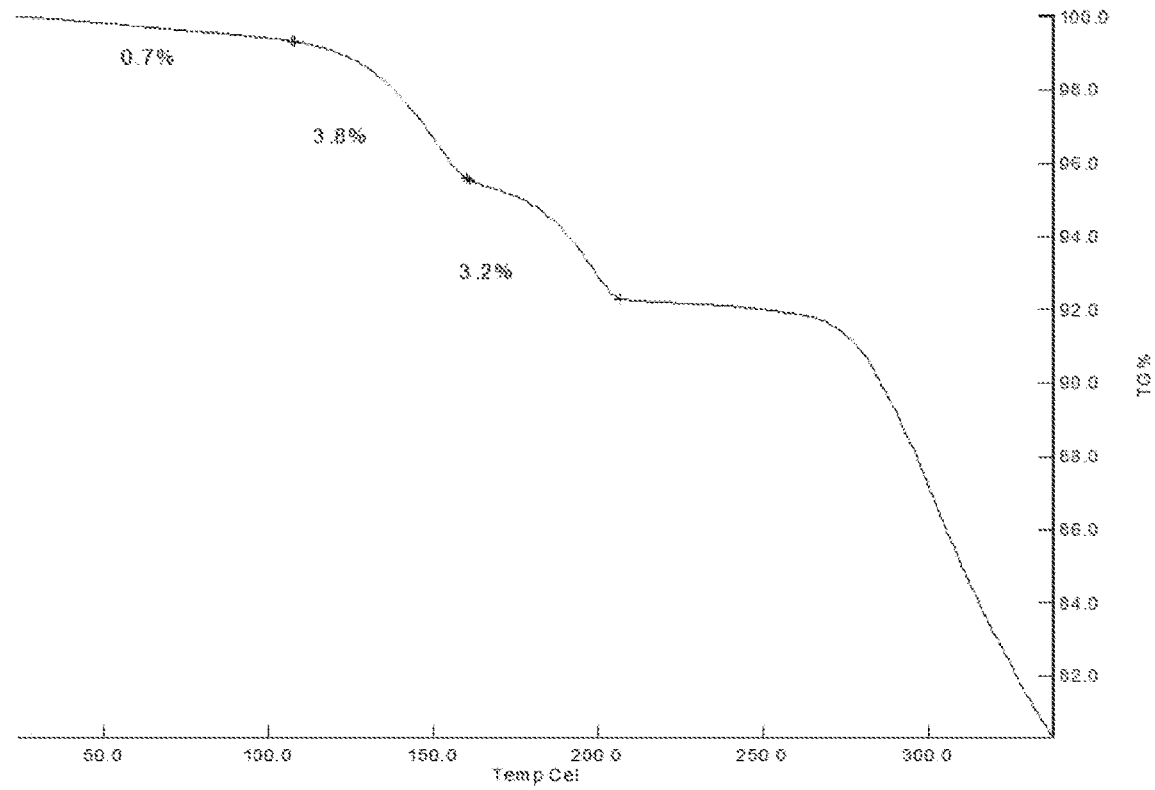
FIG. 2. Illustrates a thermogravimetric analysis (TGA) thermogram of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 1.
Figure 3:
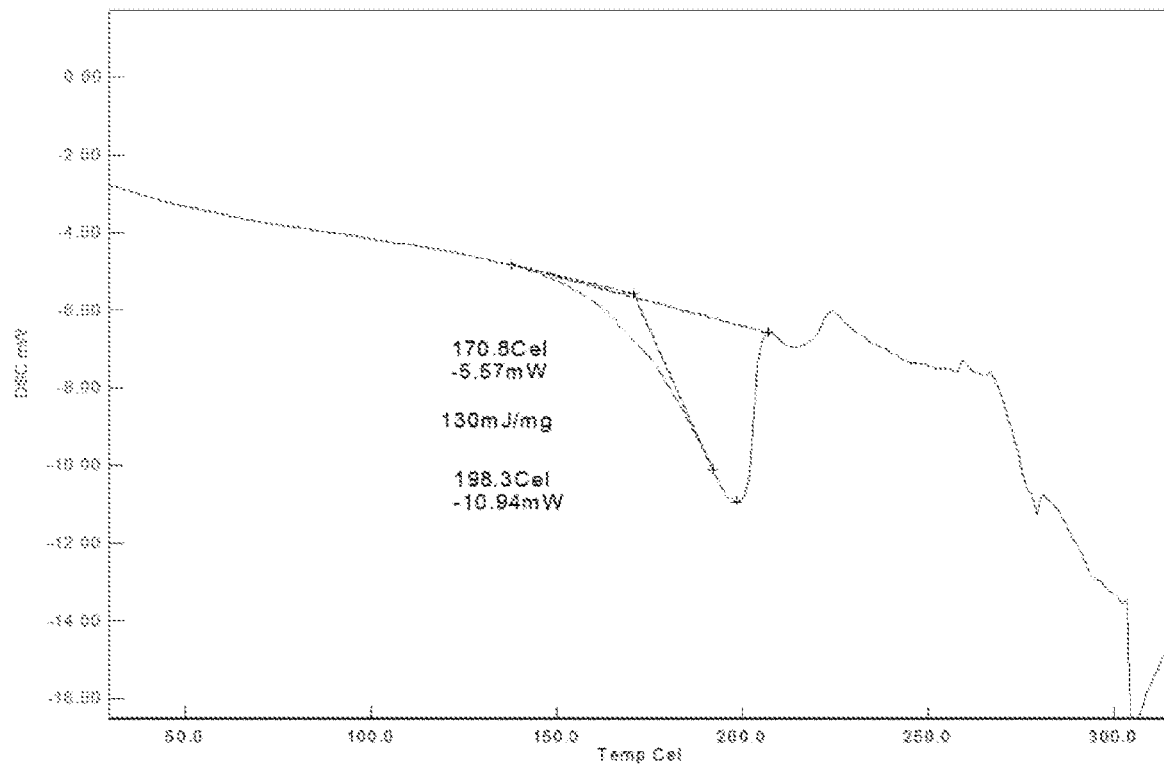
FIG. 3. Illustrates a differential scanning calorimetry (DSC) thermogram of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 1.

In some embodiments, Compound 1 is crystalline. In some embodiments, crystalline Compound 1 is Form 1 characterized as having at least one of the following properties:
(a) an X-ray powder diffraction (XRPD) pattern substantially the same as shown in FIG. 1;
(b) an X-ray powder diffraction (XRPD) pattern with characteristic peaks at 9.6° 2-Theta, 16.2° 2-Theta, 18.2° 2-Theta, 21.2° 2-Theta, 22.0° 2-Theta, and 24.8° 2-Theta;
(c) a thermogravimetric analysis (TGA) substantially similar to the one set forth in FIG. 2;
(d) a DSC thermogram substantially similar to the one set forth in FIG. 3;
(e) a DSC thermogram with an endotherm having an onset at about 171° C.;
(f) monohydrate; or
(g) combinations thereof.

In some embodiments, crystalline Compound 1, Form 1, is characterized as having at least two of the properties selected from (a) to (f). In some embodiments, crystalline Compound 1, Form 1, is characterized as having at least three of the properties selected from (a) to (f). In some embodiments, crystalline Compound 1, Form 1, is characterized as having at least four of the properties selected from (a) to (f). In some embodiments, crystalline Compound 1, Form 1, is characterized as having at least five of the properties selected from (a) to (f). In some embodiments, crystalline Compound 1, Form 1, is characterized as having properties (a) to (f).

In some embodiments, crystalline Compound 1, Form 1, has an X-ray powder diffraction (XRPD) pattern substantially the same as shown in FIG. 1. In some embodiments, crystalline Compound 1, Form 1, has an X-ray powder diffraction (XRPD) pattern with characteristic peaks at 9.6° 2-Theta, 16.2° 2-Theta, 18.2° 2-Theta, 21.2° 2-Theta, 22.0° 2-Theta, and 24.8° 2-Theta. In some embodiments, crystalline Compound 1, Form 1, has a thermogravimetric analysis (TGA) thermogram substantially similar to the one set forth in FIG. 2. In some embodiments, crystalline Compound 1, Form 1, has a DSC thermogram substantially similar to the one set forth in FIG. 3. In some embodiments, crystalline Compound 1, Form 1, has a DSC thermogram with an endotherm having an onset at about 171° C. In some embodiments, crystalline Compound 1, Form 1, is a monohydrate. In some embodiments, crystalline Compound 1, Form 1, is obtained from a combination of methanol and water (methanol/water). In some embodiments, crystalline Compound 1, Form 1, is obtained from a 40% methanol/60% water solution. In some embodiments, crystalline Compound 1, Form 1, is obtained from a 95% methanol/5% water solution. In some embodiments, crystalline Compound 1, Form 1, is solvated. In some embodiments, crystalline Compound 1, Form 1, is unsolvated.

Crystalline Compound 1, Form 2

Figure 4:
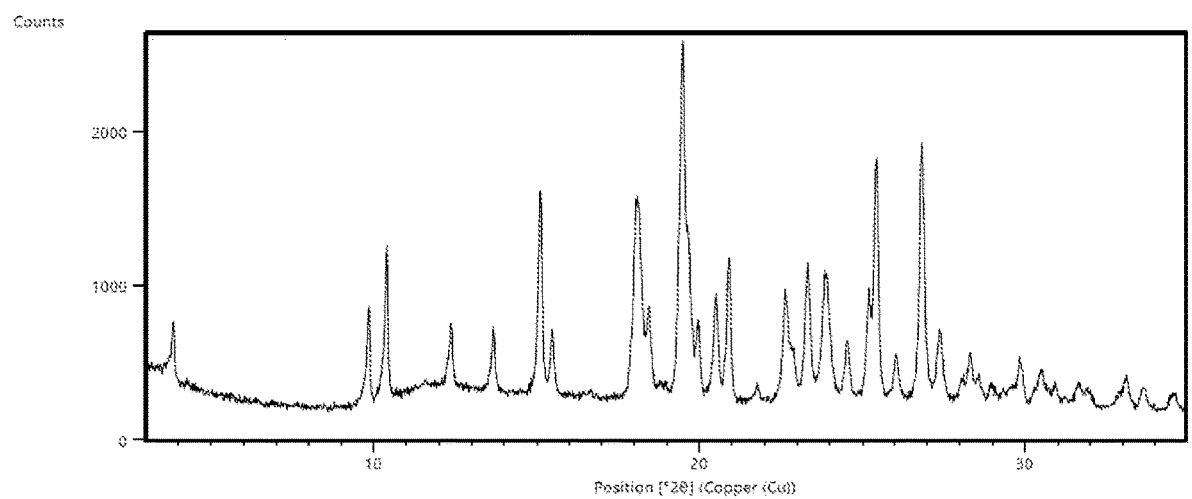
FIG. 4. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 2.
Figure 5:
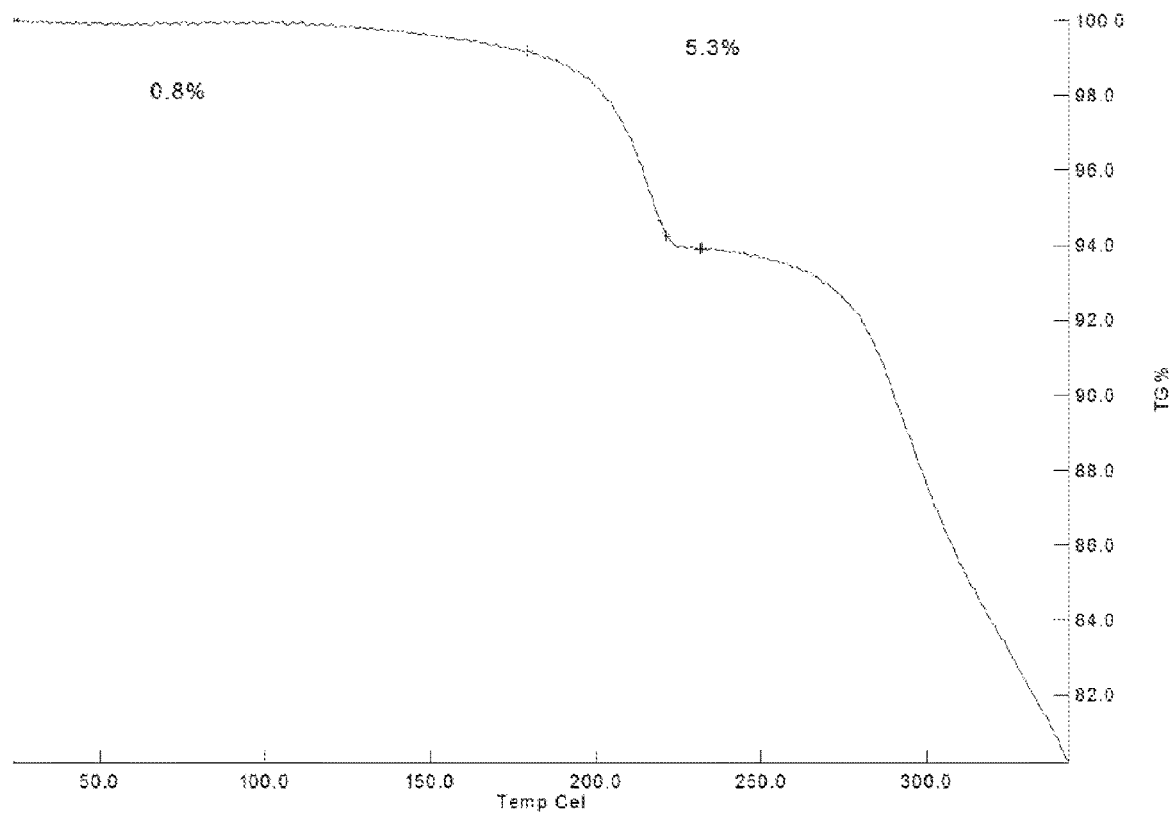
FIG. 5. Illustrates a thermogravimetric analysis (TGA) thermogram of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 2.
Figure 6:
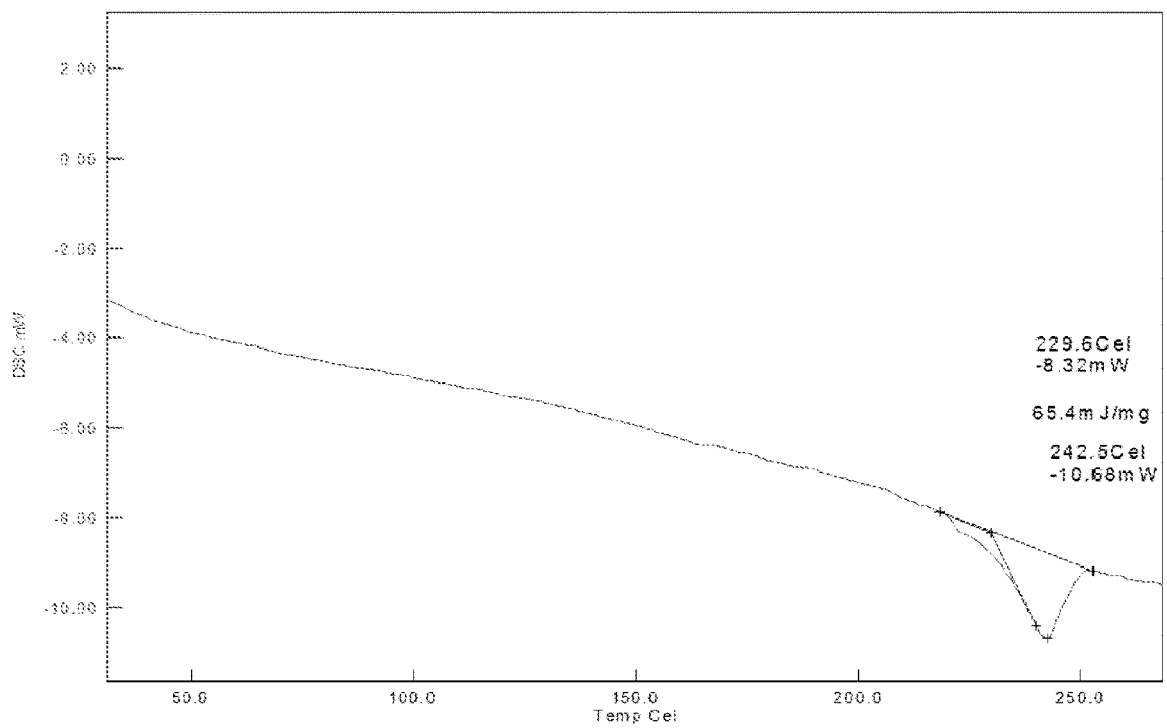
FIG. 6. Illustrates a differential scanning calorimetry (DSC) thermogram of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 2.

In some embodiments, crystalline Compound 1 is Form 2 characterized as having at least one of the following properties:
(a) an X-ray powder diffraction (XRPD) pattern substantially the same as shown in FIG. 4;
(b) an X-ray powder diffraction (XRPD) pattern with characteristic peaks at 10.4° 2-Theta, 15.1° 2-Theta, 18.0° 2-Theta, 19.5° 2-Theta, 25.4° 2-Theta, and 26.8° 2-Theta;
(c) a thermogravimetric analysis (TGA) substantially similar to the one set forth in FIG. 5;
(d) a DSC thermogram substantially similar to the one set forth in FIG. 6;
(e) a DSC thermogram with an endotherm having an onset at about 230° C.; or
(f) combinations thereof.

In some embodiments, crystalline Compound 1, Form 2, is characterized as having at least two of the properties selected from (a) to (e). In some embodiments, crystalline Compound 1, Form 2, is characterized as having at least three of the properties selected from (a) to (e). In some embodiments, crystalline Compound 1, Form 2, is characterized as having at least four of the properties selected from (a) to (e). In some embodiments, crystalline Compound 1, Form 2, is characterized as having properties (a) to (e).

In some embodiments, crystalline Compound 1, Form 2, has an X-ray powder diffraction (XRPD) pattern substantially the same as shown in FIG. 4. In some embodiments, crystalline Compound 1, Form 2, has an X-ray powder diffraction (XRPD) pattern with characteristic peaks at 10.4° 2-Theta, 15.1° 2-Theta, 18.0° 2-Theta, 19.5° 2-Theta, 25.4° 2-Theta, and 26.8° 2-Theta. In some embodiments, crystalline Compound 1, Form 2, has a thermogravimetric analysis (TGA) thermogram substantially similar to the one set forth in FIG. 5. In some embodiments, crystalline Compound 1, Form 2, has a DSC thermogram substantially similar to the one set forth in FIG. 6. In some embodiments, crystalline Compound 1, Form 2, has a DSC thermogram with an endotherm having an onset at about 230° C. In some embodiments, crystalline Compound 1, Form 2, is obtained from acetonitrile, methanol, ethanol, methyl ethyl ketone, 1-propanol, 2-propanol, or dimethylformamide. In some embodiments, crystalline Compound 1, Form 2, is obtained from acetonitrile. In some embodiments, crystalline Compound 1, Form 2, is obtained from methanol. In some embodiments, crystalline Compound 1, Form 2, is obtained from ethanol. In some embodiments, crystalline Compound 1, Form 2, is obtained from methyl ethyl ketone. In some embodiments, crystalline Compound 1, Form 2, is obtained from 1-propanol. In some embodiments, crystalline Compound 1, Form 2, is obtained from 2-propanol. In some embodiments, crystalline Compound 1, Form 2, is obtained from dimethylformamide. In some embodiments, crystalline Compound 1, Form 2, is solvated. In some embodiments, crystalline Compound 1, Form 2, is unsolvated.

Crystalline Compound 1, Form 3

Figure 7:
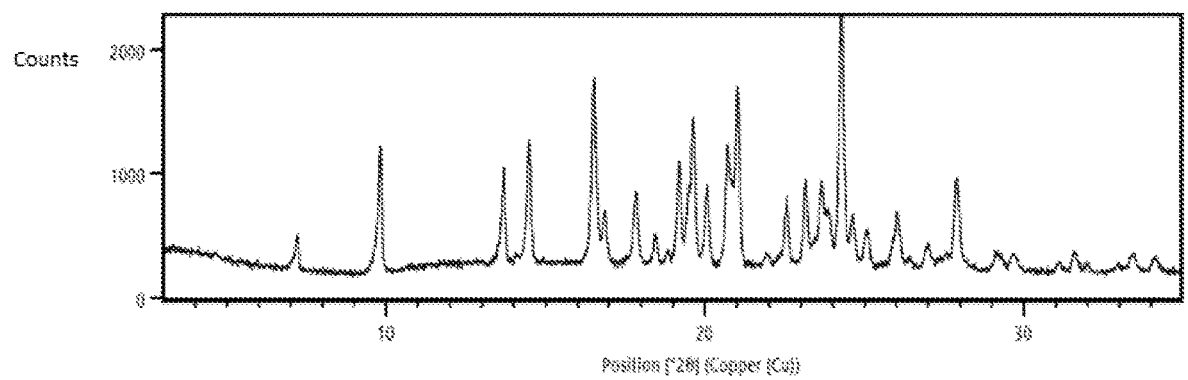
FIG. 7. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 3.

In some embodiments, crystalline Compound 1 is Form 3. In some embodiments, crystalline Compound 1, Form 3, has an X-ray powder diffraction (XRPD) pattern substantially the same as shown in FIG. 7. In some embodiments, crystalline Compound 1, Form 3, has an X-ray powder diffraction (XRPD) pattern with characteristic peaks at 9.8° 2-Theta, 14.5° 2-Theta, 16.5° 2-Theta, 19.6° 2-Theta, 20.7° 2-Theta, 21.0° 2-Theta, and 24.3° 2-Theta. In some embodiments, crystalline Compound 1, Form 1, is obtained from dimethylsulfoxide. In some embodiments, crystalline Compound 1, Form 3, is solvated. In some embodiments, crystalline Compound 1, Form 3, is unsolvated.

Crystalline Compound 1, Form 4

Figure 8:
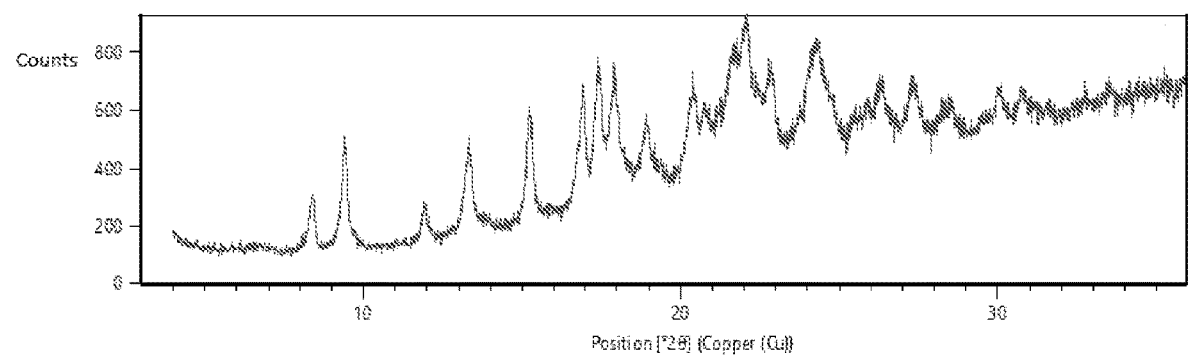
FIG. 8. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 4.

In some embodiments, crystalline Compound 1 is Form 4. In some embodiments, crystalline Compound 1, Form 4, has an X-ray powder diffraction (XRPD) pattern substantially the same as shown in FIG. 8. In some embodiments, crystalline Compound 1, Form 4, has an X-ray powder diffraction (XRPD) pattern with characteristic peaks at 9.4° 2-Theta, 15.2° 2-Theta, 16.9° 2-Theta, 17.4° 2-Theta, 17.9° 2-Theta, 21.6° 2-Theta, 22.0° 2-Theta, and 24.4° 2-Theta. In some embodiments, crystalline Compound 1, Form 1, is obtained by heating Compound 1 at 160° C. In some embodiments, crystalline Compound 1, Form 4, is solvated. In some embodiments, crystalline Compound 1, Form 4, is unsolvated.

Crystalline Compound 2, Form 1

Figure 13:
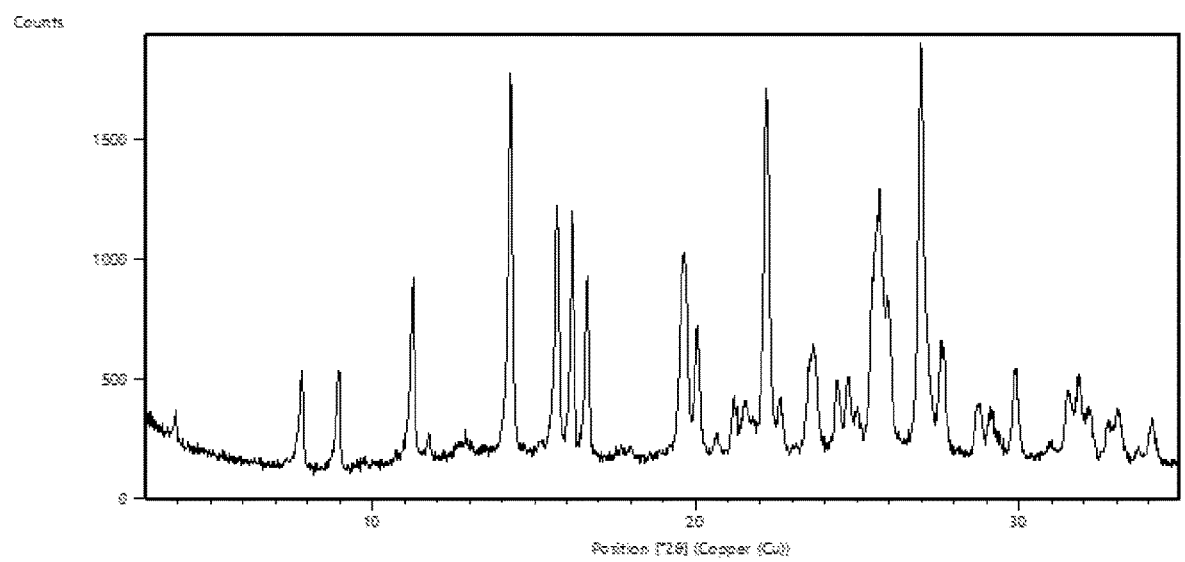
FIG. 13. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide dihydrochloride (Compound 2), Form 1.

In some embodiments, Compound 2 is crystalline. In some embodiments, crystalline Compound 2 is Form 1. In some embodiments, crystalline Compound 2, Form 1, has an X-ray powder diffraction (XRPD) pattern substantially the same as shown in FIG. 13. In some embodiments, crystalline Compound 2, Form 1, has an X-ray powder diffraction (XRPD) pattern with characteristic peaks at 14.3° 2-Theta, 15.7° 2-Theta, 16.2° 2-Theta, 22.2° 2-Theta, 25.7° 2-Theta, and 27.0° 2-Theta. In some embodiments, crystalline Compound 2, Form 1, is solvated. In some embodiments, crystalline Compound 2, Form 1, is unsolvated.

Crystalline Compound 3, Form 1

Figure 14:
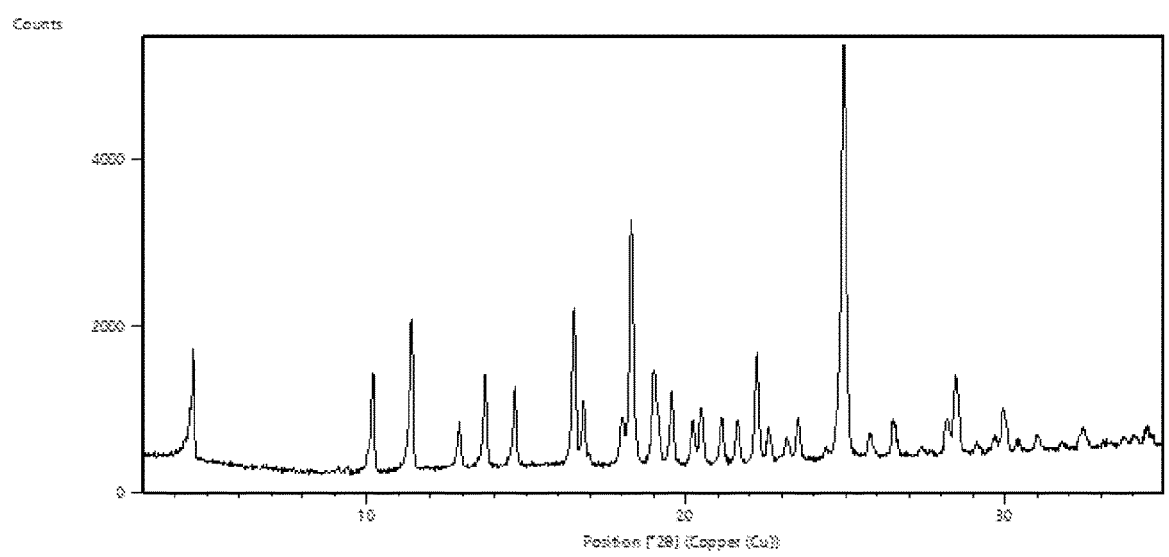
FIG. 14. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide free base (Compound 3), Form 1.

In some embodiments, Compound 3 is crystalline. In some embodiments, crystalline Compound 3 is Form 1. In some embodiments, crystalline Compound 3, Form 1 has an X-ray powder diffraction (XRPD) pattern substantially the same as shown in FIG. 14. In some embodiments, crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide free base has an X-ray powder diffraction (XRPD) pattern with characteristic peaks at 11.4° 2-Theta, 16.5° 2-Theta, 18.3° 2-Theta, 24.9° 2-Theta, and 25.0° 2-Theta. In some embodiments, crystalline Compound 3, Form 1 is solvated. In some embodiments, crystalline Compound 3, Form 1 is unsolvated.

Preparation of Crystalline Compound 1

In some embodiments, crystalline forms of Compound 1 are prepared as outlined in the Examples. It is noted that solvents, temperatures, and other reaction conditions presented herein may vary.

In certain embodiments, provided herein are methods for making a solid form of Compound 1, comprising 1) suspending Compound 1 in a solvent at a first temperature at room temperature; 2) cycling the Compound 1 mixture between ambient and a second temperature (e.g., about 40° C.) in 4 hour cycles over 72 hours; 3) collecting a solid if there is precipitation, and evaporating the solvent to collect a solid if there is no precipitation; and 4) optionally drying. In certain embodiments, provided herein are methods for making a solid form of Compound 1, comprising 1) obtaining a saturated solution of Compound 1 in a solvent; 2) adding an anti-solvent into the saturated solution; 3) cooling down to about 2-8° C. and the at about −20° C.; 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the ratio by volume of solvent and anti-solvent is about 1:4. In certain embodiments, the ratio by volume of solvent and anti-solvent is about 1:2. In certain embodiments, the ratio by volume of solvent and anti-solvent is about 1:1. In certain embodiments, the methods for making a solid form of Compound 1 are anti-solvent recrystallization experiments.

In another embodiment, crystalline Compound 1, Form 1, is substantially pure. In certain embodiments, the substantially pure crystalline Compound 1, Form 1, is substantially free of other solid forms, e.g., amorphous solid. In certain embodiments, the purity of the substantially pure crystalline Compound 1, Form 1, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 2, is substantially pure. In certain embodiments, the substantially pure crystalline Compound 1, Form 2, is substantially free of other solid forms, e.g., amorphous solid. In certain embodiments, the purity of the substantially pure crystalline Compound 1, Form 2, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 3, is substantially pure. In certain embodiments, the substantially pure crystalline Compound 1, Form 3, is substantially free of other solid forms, e.g., amorphous solid. In certain embodiments, the purity of the substantially pure crystalline Compound 1, Form 3, is no less than about 95%, no less than about 96%, no less than about 97%, no less than about 98%, no less than about 98.5%, no less than about 99%, no less than about 99.5%, or no less than about 99.8%.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. In some embodiments, solvents disclosed herein are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene.

Class 3 solvents, which possess low toxicity, include: acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine.

Residual solvents in active pharmaceutical ingredients (APIs) originate from the manufacture of APIs. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound 1 comprise an organic solvent(s). In some embodiments, compositions comprising Compound 1 comprise a residual amount of an organic solvent(s). In some embodiments, compositions comprising Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine. In some embodiments, the Class 3 solvent is selected from the group consisting of acetone, ethyl acetate, isopropyl acetate, tert-butyl methyl ether, heptane, isopropanol, and ethanol.

In some embodiments, compositions comprising Compound 1, 2, or 3 comprise a residual amount of a Class 2 solvent. In some embodiments, the organic solvent is a Class 2 solvent. In some embodiments, the Class 2 solvent is selected from the group consisting of acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene. In some embodiments, the Class 2 solvent is selected from the group consisting of acetonitrile, tetrahydrofuran, and toluene. In some embodiments, the Class 2 solvent is acetonitrile.

In some embodiments, compositions comprising Compound 1, 2, or 3 comprise a residual amount of a solvent for which no adequate toxicological data were found. In some embodiments, the organic solvent is a solvent for which no adequate toxicological data were found. In some embodiments, the solvent is selected from the group consisting of 2-butanone and 2-methyltetrahydrofuran.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. The term "about" when referring to a number or a numerical range means that the number or numerical range referred to is an approximation within experimental variability (or within statistical experimental error), and thus the number or numerical range may vary between 1% and 15% of the stated number or numerical range.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of Compound 1, 2, or 3 dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which Compound 1, 2, or 3 is absorbed into the general circulation when the pharmaceutical composition is taken orally as compared to intravenous injection.

"Blood plasma concentration" refers to the concentration of Compound 1, 2, or 3 in the plasma component of blood of a subject. It is understood that the plasma concentration of Compound 1, 2, or 3 may vary significantly between subjects, due to variability with respect to metabolism and/or possible interactions with other therapeutic agents. In accordance with one embodiment disclosed herein, the blood plasma concentration of Compound 1, 2, or 3 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1, 2, or 3 may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, 2, or 3, age, weight, general condition of the subject, the condition being treated, the severity of the condition being treated, and the judgment of the prescribing physician. By way of example only, therapeutically effective amounts may be determined by a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder, or condition. An "enhancing-effective amount," as used herein, refers to an amount adequate to enhance the effect of a therapeutic agent in the treatment of a disease, disorder, or condition. When used in a patient, amounts effective for this use will depend on the severity and course of the disease, disorder, or condition, previous therapy, the patient's health status and response to the drugs, and the judgment of the treating physician.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. As an example, one can determine such prophylactically effective amounts by a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, $IC_{50}$ refers to a dosage, concentration or amount of a particular test compound that elicits a dose-dependent response at 50% of maximal expression of a particular response that is induced, provoked or potentiated by the particular test compound.

Methods

In some embodiments of the methods of using crystalline Compound 1 as described herein, is a method of treating a disease or condition associated with RSK activity in a mammal, wherein the method comprises administering to the mammal a therapeutically effective amount of crystalline Compound 1. In some embodiments is a method of treating a disease or condition associated with p90 ribosomal S6 kinase (RSK) activity in a mammal, wherein the method comprises administering to the mammal a therapeutically effective amount of a crystalline form of Compound 1 described herein. In some embodiments is a method of treating a disease or condition associated with p90 ribosomal S6 kinase (RSK) activity in a mammal, wherein the method comprises administering to the mammal a therapeutically effective amount of a crystalline form of Compound 1 described herein; wherein the disease or condition is cancer. In some embodiments is a method of treating cancer in a mammal, wherein the method comprises administering to the mammal a therapeutically effective amount of a crystalline form of Compound 1 described herein; wherein the cancer is breast cancer, prostate cancer, lung cancer, brain cancer, skin cancer, bone cancer, ovarian cancer, or a blood cancer. In some embodiments is a method of treating prostate cancer in a mammal, wherein the method comprises administering to the mammal a therapeutically effective amount of a crystalline form of Compound 1 described herein. In some embodiments is a method of treating lung cancer in a mammal, wherein the method comprises administering to the mammal a therapeutically effective amount of a crystalline form of Compound 1 described herein. In some embodiments is a method of treating brain cancer in a mammal, wherein the method comprises administering to the mammal a therapeutically effective amount of a crystalline form of Compound 1 described herein. In some embodiments is a method of treating skin cancer in a mammal, wherein the method comprises administering to the mammal a therapeutically effective amount of a crystalline form of Compound 1 described herein. In some embodiments is a method of treating bone cancer in a mammal, wherein the method comprises administering to the mammal a therapeutically effective amount of a crystalline form of Compound 1 described herein. In some embodiments is a method of treating ovarian cancer in a mammal, wherein the method comprises administering to the mammal a therapeutically effective amount of a crystalline form of Compound 1 described herein. In some embodiments is a method of treating a blood cancer in a mammal, wherein the method comprises administering to the mammal a therapeutically effective amount of a crystalline form of Compound 1 described herein. In some embodiments is a method of treating breast cancer in a mammal, wherein the method comprises administering to the mammal a therapeutically effective amount of a crystalline form of Compound 1 described herein. In some embodiments is a method of treating breast cancer in a mammal, wherein the method comprises administering to the mammal a therapeutically effective amount of a crystalline form of Compound 1 described herein; wherein the breast cancer is selected from Luminal A, Luminal B, Her-2 positive, triple-negative breast cancer, basal-like breast cancer, inflammatory breast cancer, BRCA1/2 mutated breast cancer, drug resistant breast cancer, murine breast cancer, gefitinib insensitive: MDA-MB-231, and metastatic breast cancer. In some embodiments of the methods described herein, the crystalline form of Compound 1 is Form 1 described herein. In some embodiments of the methods described herein, the crystalline form of Compound 1 is Form 2 described herein. In some embodiments of the methods described herein, the crystalline form of Compound 1 is Form 3 described herein. In some embodiments of the methods described herein, the crystalline form of Compound 1 is Form 4 described herein.

In some embodiments of the methods of using crystalline Compound 2 as described herein, is a method of treating a disease or condition associated with RSK activity in a mammal, wherein the method comprises administering to the mammal a therapeutically effective amount of crystalline Compound 2. In some embodiments is a method of treating a disease or condition associated with p90 ribosomal S6 kinase (RSK) activity in a mammal, wherein the method comprises administering to the mammal a therapeutically effective amount of a crystalline form of Compound 2 described herein. In some embodiments is a method of treating a disease or condition associated with p90 ribosomal S6 kinase (RSK) activity in a mammal, wherein the method comprises administering to the mammal a therapeutically effective amount of a crystalline form of Compound 2 described herein; wherein the disease or condition is cancer. In some embodiments is a method of treating cancer in a mammal, wherein the method comprises administering to the mammal a therapeutically effective amount of a crystalline form of Compound 2 described herein; wherein the cancer is breast cancer, prostate cancer, lung cancer, brain cancer, skin cancer, bone cancer, ovarian cancer, or a blood cancer. In some embodiments is a method of treating prostate cancer in a mammal, wherein the method comprises administering to the mammal a therapeutically effective amount of a crystalline form of Compound 2 described herein. In some embodiments is a method of treating lung cancer in a mammal, wherein the method comprises administering to the mammal a therapeutically effective amount of a crystalline form of Compound 2 described herein. In some embodiments is a method of treating brain cancer in a mammal, wherein the method comprises administering to the mammal a therapeutically effective amount of a crystalline form of Compound 2 described herein. In some embodiments is a method of treating skin cancer in a mammal, wherein the method comprises administering to the mammal a therapeutically effective amount of a crystalline form of Compound 2 described herein. In some embodiments is a method of treating bone cancer in a mammal, wherein the method comprises administering to the mammal a therapeutically effective amount of a crystalline form of Compound 2 described herein. In some embodiments is a method of treating ovarian cancer in a mammal, wherein the method comprises administering to the mammal a therapeutically effective amount of a crystalline form of Compound 2 described herein. In some embodiments is a method of treating a blood cancer in a mammal, wherein the method comprises administering to the mammal a therapeutically effective amount of a crystalline form of Compound 2 described herein. In some embodiments is a method of treating breast cancer in a mammal, wherein the method comprises administering to the mammal a therapeutically effective amount of a crystalline form of Compound 2 described herein. In some embodiments is a method of treating breast cancer in a mammal, wherein the method comprises administering to the mammal a therapeutically effective amount of a crystalline form of Compound 2 described herein; wherein the breast cancer is selected from Luminal A, Luminal B, Her-2 positive, triple-negative breast cancer, basal-like breast cancer, inflammatory breast cancer, BRCA1/2 mutated breast cancer, drug resistant breast cancer, murine breast cancer, gefitinib insensitive: MDA-MB-231, and metastatic breast cancer. In some embodiments of the methods described herein, the crystalline form of Compound 2 is Form 1 described herein.

In some embodiments of the methods of using crystalline Compound 3 as described herein, is a method of treating a disease or condition associated with RSK activity in a mammal, wherein the method comprises administering to the mammal a therapeutically effective amount of crystalline Compound 3. In some embodiments is a method of treating a disease or condition associated with p90 ribosomal S6 kinase (RSK) activity in a mammal, wherein the method comprises administering to the mammal a therapeutically effective amount of a crystalline form of Compound 3 described herein. In some embodiments is a method of treating a disease or condition associated with p90 ribosomal S6 kinase (RSK) activity in a mammal, wherein the method comprises administering to the mammal a therapeutically effective amount of a crystalline form of Compound 3 described herein; wherein the disease or condition is cancer. In some embodiments is a method of treating cancer in a mammal, wherein the method comprises administering to the mammal a therapeutically effective amount of a crystalline form of Compound 3 described herein; wherein the cancer is breast cancer, prostate cancer, lung cancer, brain cancer, skin cancer, bone cancer, ovarian cancer, or a blood cancer. In some embodiments is a method of treating prostate cancer in a mammal, wherein the method comprises administering to the mammal a therapeutically effective amount of a crystalline form of Compound 3 described herein. In some embodiments is a method of treating lung cancer in a mammal, wherein the method comprises administering to the mammal a therapeutically effective amount of a crystalline form of Compound 3 described herein. In some embodiments is a method of treating brain cancer in a mammal, wherein the method comprises administering to the mammal a therapeutically effective amount of a crystalline form of Compound 3 described herein. In some embodiments is a method of treating skin cancer in a mammal, wherein the method comprises administering to the mammal a therapeutically effective amount of a crystalline form of Compound 3 described herein. In some embodiments is a method of treating bone cancer in a mammal, wherein the method comprises administering to the mammal a therapeutically effective amount of a crystalline form of Compound 3 described herein. In some embodiments is a method of treating ovarian cancer in a mammal, wherein the method comprises administering to the mammal a therapeutically effective amount of a crystalline form of Compound 3 described herein. In some embodiments is a method of treating a blood cancer in a mammal, wherein the method comprises administering to the mammal a therapeutically effective amount of a crystalline form of Compound 3 described herein. In some embodiments is a method of treating breast cancer in a mammal, wherein the method comprises administering to the mammal a therapeutically effective amount of a crystalline form of Compound 3 described herein. In some embodiments is a method of treating breast cancer in a mammal, wherein the method comprises administering to the mammal a therapeutically effective amount of a crystalline form of Compound 3 described herein; wherein the breast cancer is selected from Luminal A, Luminal B, Her-2 positive, triple-negative breast cancer, basal-like breast cancer, inflammatory breast cancer, BRCA1/2 mutated breast cancer, drug resistant breast cancer, murine breast cancer, gefitinib insensitive: MDA-MB-231, and metastatic breast cancer. In some embodiments of the methods described herein, the crystalline form of Compound 3 is Form 1 described herein.

Combination Treatments

In some embodiments, the crystalline forms of Compound 1, 2, or 3 described herein, and compositions thereof, are used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In some embodiments, it is appropriate to administer a crystalline form of Compound 1, 2, or 3 described herein in combination with another therapeutic agent. By way of example only, if one of the side effects experienced by a patient upon receiving a crystalline form of Compound 1, 2, or 3 described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

For therapeutic applications, in some embodiments the compounds or drugs of the present invention are administered alone or co-administered in combination with conventional chemotherapy, radiotherapy, hormonal therapy, and/or immunotherapy.

As a non-limiting example, in some embodiments the crystalline forms of Compound 1, 2, or 3 described herein are co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

In some embodiments, the crystalline forms of Compound 1, 2, or 3 described herein are co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

In some embodiments, the crystalline forms of Compound 1, 2, or 3 described herein are co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I etc.).

In further embodiments, the crystalline forms of Compound 1, 2, or 3 described herein are co-administered with a poly ADP-ribose polymerase (PARP) inhibitor, STAT 3 inhibitor, Janus Kinase inhibitor, or EGFR inhibitor.

The particular choice of compounds used will depend upon the diagnosis of the attending physicians and their judgment of the condition of the patient and the appropriate treatment protocol. In some embodiments, the compounds are administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a crystalline form of Compound 1, 2, or 3 described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In some embodiments, the compounds described herein are used in combination with procedures that may provide additional or synergistic benefit to the patient. In some embodiments, the crystalline forms of Compound 1, 2, or 3 described herein are administered with radiation therapy. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies are administered before, during or after the occurrence of a disease or condition, and the timing of administering the composition containing a compound can vary. Thus, for example, in some embodiments the compounds are used as a prophylactic and are administered continuously to subjects with a propensity to develop conditions or diseases in order to prevent the occurrence of the disease or condition. In some embodiments, the compounds and compositions can be administered to a subject during or as soon as possible after the onset of the symptoms. In some embodiments, the administration of the compounds is initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof.

A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Pharmaceutical Compositions and Administration

Also described herein are pharmaceutical composition containing the compounds disclosed herein. In one embodiment, the present invention relates to a composition comprising compounds described herein in a pharmaceutically acceptable carrier, excipient or diluent and in an amount effective to inhibit the activity of RSK when administered to an animal, preferably a mammal, most preferably a human patient.

In some embodiments is a pharmaceutical composition comprising a crystalline form of Compound 1 described herein, and at least one pharmaceutically acceptable excipient. In some embodiments is a pharmaceutical composition comprising crystalline Compound 1, Form 1 described herein, and at least one inactive ingredient selected from pharmaceutically acceptable carriers, diluents, and excipients. In some embodiments is a pharmaceutical composition comprising crystalline Compound 1, Form 2 described herein, and at least one inactive ingredient selected from pharmaceutically acceptable carriers, diluents, and excipients. In some embodiments is a pharmaceutical composition comprising crystalline Compound 1, Form 3 described herein, and at least one inactive ingredient selected from pharmaceutically acceptable carriers, diluents, and excipients. In some embodiments is a pharmaceutical composition comprising crystalline Compound 1, Form 4 described herein, and at least one inactive ingredient selected from pharmaceutically acceptable carriers, diluents, and excipients.

In some embodiments is a pharmaceutical composition comprising a crystalline form of Compound 2 described herein, and at least one pharmaceutically acceptable excipient. In some embodiments is a pharmaceutical composition comprising crystalline Compound 2, Form 1 described herein, and at least one inactive ingredient selected from pharmaceutically acceptable carriers, diluents, and excipients.

In some embodiments is a pharmaceutical composition comprising a crystalline form of Compound 3 described herein, and at least one pharmaceutically acceptable excipient. In some embodiments is a pharmaceutical composition comprising crystalline Compound 3, Form 1 described herein, and at least one inactive ingredient selected from pharmaceutically acceptable carriers, diluents, and excipients.

A pharmaceutical composition, as used herein, refers to a mixture of a crystalline form of Compound 1, 2, or 3 described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The crystalline forms of Compound 1, 2, or 3 described herein can be used singly or in combination with one or more therapeutic agents as components of mixtures (as in combination therapy).

Administration of a crystalline form of Compound 1, 2, or 3 described herein, in pure form or in an appropriate pharmaceutical composition, can be carried out via any of the accepted modes of administration of agents for serving similar utilities. The pharmaceutical compositions described herein can be prepared by combining a crystalline form of Compound 1, 2, or 3 described herein with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions described herein are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a crystalline form of Compound 1, 2, or 3 described herein in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a crystalline form of Compound 1, 2, or 3 described herein for treatment of a disease or condition of interest described herein.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

In some embodiments, a pharmaceutical composition described herein is in the form of a solid or liquid. In one aspect, the carrier(s) are particulate, so that the compositions are, for example, in tablet or powder form. In some embodiments, the carrier(s) is liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

In some embodiments, as a solid composition for oral administration, the pharmaceutical composition is formulated into a powder, granule, compressed tablet, pill, capsule, chewing gum, wafer or the like form. Such a solid composition will typically contain one or more inert diluents or edible carriers. In some embodiments, one or more of the following is present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

In some embodiments, the pharmaceutical composition is in the form of a liquid, for example, an elixir, syrup, solution, emulsion or suspension. In some embodiments, the liquid is for oral administration or for delivery by injection, as two examples. When intended for oral administration, preferred composition contain, in addition to the present compounds, one or more of a sweetening agent, preservatives, dye/colorant and flavor enhancer. In some embodiments, in a composition intended to be administered by injection, one or more of a surfactant, preservative, wetting agent, dispersing agent, suspending agent, buffer, stabilizer and isotonic agent is included.

The liquid pharmaceutical compositions described herein, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition described herein intended for either parenteral or oral administration should contain an amount of a crystalline form of Compound 1, 2, or 3 described herein such that a suitable dosage will be obtained. Typically, this amount is at least 0.01% of a crystalline form of Compound 1, 2, or 3 described herein in the composition. When intended for oral administration, this amount may be varied to be between 0.1 and about 70% of the weight of the composition. Preferred oral pharmaceutical compositions contain between about 4% and about 50% of the crystalline form of Compound 1, 2, or 3 described herein. Preferred pharmaceutical compositions and preparations according to the present invention are prepared so that a parenteral dosage unit contains between 0.01 to 10% by weight of the crystalline form of Compound 1, 2, or 3 described herein prior to dilution.

In some embodiments, the pharmaceutical composition described herein is intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. In some embodiments, thickening agents are present in a pharmaceutical composition for topical administration. In some embodiments intended for transdermal administration, the composition includes a transdermal patch or iontophoresis device. In some embodiments, topical formulations contain a concentration of the crystalline form of Compound 1, 2, or 3 described herein from about 0.1 to about 10% w/v (weight per unit volume).

In some embodiments, the pharmaceutical composition described herein is intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition described herein may include various materials, which modify the physical form of a solid or liquid dosage unit. For example, the composition may include materials that form a coating shell around the active ingredients. In some embodiments, the materials that form the coating shell are typically inert, and are selected from, for example, sugar, shellac, and other enteric coating agents. Alternatively, in some embodiments, the active ingredients are encased in a gelatin capsule.

The pharmaceutical composition described herein in solid or liquid form may include an agent that binds to the crystalline form of Compound 1, 2, or 3 described herein and thereby assists in the delivery of the compound. Suitable agents that may act in this capacity include a monoclonal or polyclonal antibody, a protein or a liposome.

The pharmaceutical composition described herein may consist of dosage units that can be administered as an aerosol. The term aerosol is used to denote a variety of systems ranging from those of colloidal nature to systems consisting of pressurized packages. In some embodiments, delivery is by a liquefied or compressed gas or by a suitable pump system that dispenses the active ingredients. In some embodiments, aerosols of a crystalline form of Compound 1, 2, or 3 described herein are delivered in single phase, bi-phasic, or tri-phasic systems in order to deliver the active ingredient(s). Delivery of the aerosol includes the necessary container, activators, valves, subcontainers, and the like, which together may form a kit.

In some embodiments, the pharmaceutical compositions described herein are prepared by methodology well known in the pharmaceutical art. For example, in some embodiments, a pharmaceutical composition intended to be administered by injection is prepared by combining a crystalline form of Compound 1, 2, or 3 described herein with sterile, distilled water so as to form a solution. In some embodiments, a surfactant is added to facilitate the formation of a homogeneous solution or suspension. Surfactants are compounds that non-covalently interact with the crystalline form of Compound 1, 2, or 3 described herein so as to facilitate dissolution or homogeneous suspension of the compound in the aqueous delivery system.

In some embodiments, the pharmaceutical compositions described herein are formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

In some embodiments, the pharmaceutical compositions described herein are delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

In some embodiments, the pharmaceutical compositions described herein also relate to an intravaginal shell or core drug delivery device suitable for administration to the human or animal female. In some embodiments, the device is comprised of the active pharmaceutical ingredient in a polymer matrix, surrounded by a sheath, and capable of releasing the compound in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intraocular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the crystalline forms of Compound 1, 2, or 3 described herein to a subject in need thereof.

Methods of Dosing and Treatment Regimens

The crystalline forms of Compound 1, 2, or 3 described herein can be used in the preparation of medicaments for the treatment of cancer, or for the treatment of diseases or conditions that would benefit, at least in part, from RSK inhibition. In addition, a method for treating any of the diseases or conditions described herein in a subject in need of such treatment, involves administration of pharmaceutical compositions containing a crystalline form of Compound 1, 2, or 3 described herein in therapeutically effective amounts to said subject.

The crystalline forms of Compound 1, 2, or 3 described herein, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g). In some embodiments, the daily dosages appropriate for the crystalline forms of Compound 1, 2, or 3 described herein are from about 0.01 mg/kg to about 20 mg/kg. In some embodiments, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. In some embodiments, suitable unit dosage forms for oral administration include from about 1 to about 500 mg active ingredient. In some embodiments, the unit dosage is about 1 mg, about 5 mg, about, 10 mg, about 20 mg, about 50 mg, about 100 mg, about 200 mg, about 250 mg, about 400 mg, or about 500 mg.

The ranges of effective doses provided herein are not intended to be limiting and represent preferred dose ranges. Such dosages may be altered depending on a number of variables, not limited to the activity of the compound used, the disease or condition to be treated, the mode of administration, the requirements of the individual subject, the severity of the disease or condition being treated, and the judgment of the practitioner. However, the most preferred dosage will be tailored to the individual subject, as is understood and determinable by one skilled in the relevant arts. (see, e.g., Berkow et al., eds., *The Merck Manual*, 16$^{th}$ edition, Merck and Co., Rahway, N.J., 1992; Goodman et al, eds., *Goodman and Cilman's The Pharmacological Basis of Therapeutics*, 10$^{th}$ edition, Pergamon Press, Inc., Elmsford, N.Y., (2001); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985); Osolci et al, eds., *Remington's Pharmaceutical Sciences*, 18$^{th}$ edition, Mack Publishing Co., Easton, PA (1990); Katzung, *Basic and Clinical Pharmacology*, Appleton and Lange, Norwalk, CT (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions described herein can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

The compositions containing the crystalline forms of Compound 1, 2, or 3 described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the crystalline forms of Compound 1, 2, or 3, in some embodiments, is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the crystalline forms of Compound 1, 2, or 3, in some embodiments, is given continuously; alternatively, in some embodiments, the dose of drug being administered is temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. In some embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

In some embodiments, the pharmaceutical composition described herein is in unit dosage forms suitable for single administration of precise dosages. In unit dosage form, the formulation is divided into unit doses containing appropriate quantities of one or more compound. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, in some embodiments, multiple-dose reclosable containers are used, in which case it is typical to include a preservative in the composition. By way of example only, in some embodiments, formulations for parenteral injection are presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the ED$_{50}$ with minimal toxicity. The dosage may vary within this range depending upon the dosage form employed and the route of administration utilized.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. No. 5,323, 907. Examples of pharmaceutical packaging materials include, but are not limited to, blister packs, bottles, tubes, bags, containers, bottles, and any packaging material suitable for a selected formulation and intended mode of administration and treatment.

In some embodiments, the crystalline forms of Compound 1, 2, or 3 described herein, are presented in a package or dispenser device which may contain one or more unit dosage forms containing the active ingredient. The crystalline form of Compound 1, 2, or 3 described herein is packaged alone, or packaged with another compound or another ingredient or additive. In some embodiments, the package contains one or more containers filled with one or more of the ingredients of the pharmaceutical compositions. In some embodiments, the package comprises metal or plastic foil, such as a blister pack. In some embodiments, the package or dispenser is accompanied with a notice associated with the container in form prescribed by a governmental agency regulating the manufacture, use, or sale of pharmaceuticals, which notice is reflective of approval by the agency of the form of the drug for human or veterinary administration. In some embodiments, such notice, for example, is the labeling approved by the U.S. Food and Drug Administration for prescription drugs, or the approved product insert. In some embodiments, compositions include a crystalline form of Compound 1, 2, or 3 described herein formulated in a compatible pharmaceutical carrier are prepared, placed in an appropriate container, and labeled for treatment of an indicated condition.

For example, the container(s) include crystalline Compound 1, 2, or 3, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a crystalline form of Compound 1, 2, or 3 formulated in a compatible pharmaceutical carrier are also prepared, placed in an appropriate container, and labeled for treatment of an indicated condition.

EXAMPLES

List of Abbreviations

As used throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
eq or equiv equivalent(s)
Et ethyl
$Et_2O$ diethyl ether
EtOH ethanol
EtOAc ethyl acetate
HPLC high performance liquid chromatography
Me methyl
MEK methyl ethyl ketone
MeOH methanol
MS mass spectroscopy
GC gas chromatography
h hour(s)
KF Karl Fischer
min minutes
MsOH methanesulfonic acid
NMR nuclear magnetic resonance
RP-HPLC reverse phase-high performance liquid chromatography
r.t. room temperature
TFA trifluoroacetic acid
THF tetrahydrofuran
TLC thin layer chromatography
V volumes I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: Preparation of Compounds 1, 2, and 3

The preparation of Compounds 1, 2, and 3 is disclosed in U.S. Pat. No. 9,771,366, the content of which is incorporated by reference in its entirety.

II. Characterization of Polymorphs

Example 2: X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analysed using Cu K radiation (α1 λ=1.54060 Å; α2=1.54443 Å; β=1.39225 Å; α1: α2 ratio=0.5) running in transmission mode (step size 0.0130° 2θ) using 40 kV/40 mA generator settings.

XRPD analysis of Form 1 of Compound 1 (FIG. 1) showed Form 1 to be crystalline with characteristic peaks at 9.6° 2-Theta, 16.2° 2-Theta, 18.2° 2-Theta, 21.2° 2-Theta, 22.0° 2-Theta, and 24.8° 2-Theta.

XRPD analysis of Form 2 of Compound 1 (FIG. 4) showed Form 2 to be crystalline with characteristic peaks at 10.4° 2-Theta, 15.1° 2-Theta, 18.0° 2-Theta, 19.5° 2-Theta, 25.4° 2-Theta, and 26.8° 2-Theta.

XRPD analysis of Form 3 of Compound 1 (FIG. 7) showed Form 3 to be crystalline with characteristic peaks at 9.8° 2-Theta, 14.5° 2-Theta, 16.5° 2-Theta, 19.6° 2-Theta, 20.7° 2-Theta, 21.0° 2-Theta, and 24.3° 2-Theta.

XRPD analysis of Form 4 of Compound 1 (FIG. 8) showed Form 4 to be crystalline with characteristic peaks at 9.4° 2-Theta, 15.2° 2-Theta, 16.9° 2-Theta, 17.4° 2-Theta, 17.9° 2-Theta, 21.6° 2-Theta, 22.0° 2-Theta, and 24.4° 2-Theta.

XRPD analysis of Form 1 of Compound 2 (FIG. 13) showed it to be crystalline with characteristic peaks at 14.3° 2-Theta, 15.7° 2-Theta, 16.2° 2-Theta, 22.2° 2-Theta, 25.7° 2-Theta, and 27.0° 2-Theta.

XRPD analysis of Form 1 of Compound 3 (FIG. 14) showed it to be crystalline with characteristic peaks at 11.4° 2-Theta, 16.5° 2-Theta, 18.3° 2-Theta, 24.9° 2-Theta, and 25.0° 2-Theta.

Example 3: Polarized Light Microscopy (PLM)

Light microscopy studies were performed using an Olympus BX50 polarising microscope, equipped with a Motic camera and image capture software (Motic Images Plus 2.0).

PLM analysis of Form 1 of Compound 1 showed the material to be birefrigent with small, agglomerated particles and no clear morphology.

PLM analysis of Form 2 of Compound 1 showed the material to be birefrigent with small, agglomerated particles and no clear morphology.

Example 4: Thermogravimetric Analysis (TGA)

Approximately, 5 mg of material was weighed into an open aluminum pan and loaded into a simultaneous thermogravimetric/differential thermal analyser (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm3/min.

TGA of Form 1 of Compound 1 (FIG. 2) showed from the onset of heating there was a series of small mass losses of (0.7%, 3.8% and 3.2%) by TG corresponding the surface solvent loss, loss of one equivalent of water and the loss of HCl, until approx. 280° C. where sample degradation was observed.

TGA of Form 2 of Compound 1 (FIG. 5) showed one small mass loss of 0.8% from the start of the experiment to about 232° C. A second, larger mass loss of 5.3% was observed at 232° C.

Example 5: Differential Scanning Calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 350° C. at a scan rate of 10° C./min and the resulting heat flow response monitored. Nitrogen was used as the purge gas, at a flow rate of 50 cm3/min. A second DSC experiment was performed where the sample and reference were heated to a lower temperature of 300° C. All other parameters remained the same.

DSC analysis of Form 1 of Compound 1 (FIG. 3) showed a sharp melting endotherm with onset at 171° C. (81 J/g).

DSC analysis of Form 2 of Compound 1 (FIG. 6) showed a sharp melting endotherm with onset at 240° C. (77 J/g).

Example 6: Dynamic Vapor Sorption (DVS)

Approximately, 10-20 mg of sample was placed into a mesh vapour sorption balance pan and loaded into a DVS Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Figure 9:
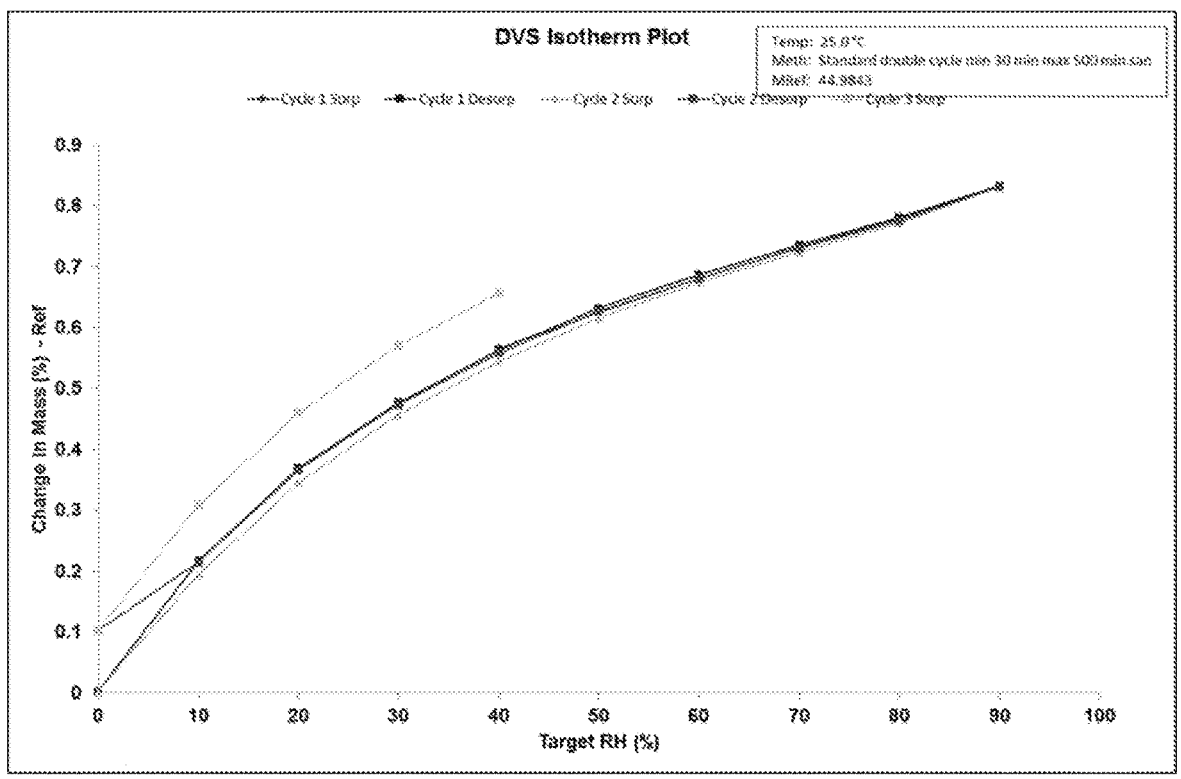
FIG. 9. Illustrates a gravimetric vapor sorption (GVS) analysis of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 1.
Figure 10:
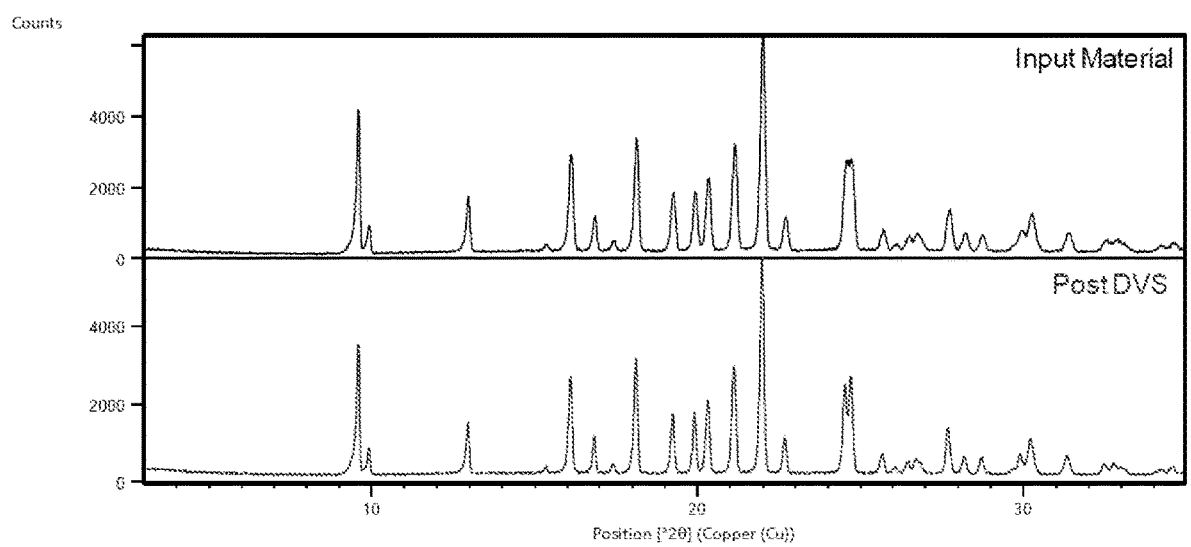
FIG. 10. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1) Form 1, pre-GVS and post-GVS.

The DVS analysis of Form 1 of Compound 1 (FIG. 9) showed that the material was slightly hygroscopic with a +0.8% change in mass at 90% RH or 0.2 equiv. of water. Post-DVS XRPD analysis showed that the material remained as Form 1 after exposure to DVS humidity conditions indicating the crystallised water remained within the lattice (FIG. 10).

Figure 11:
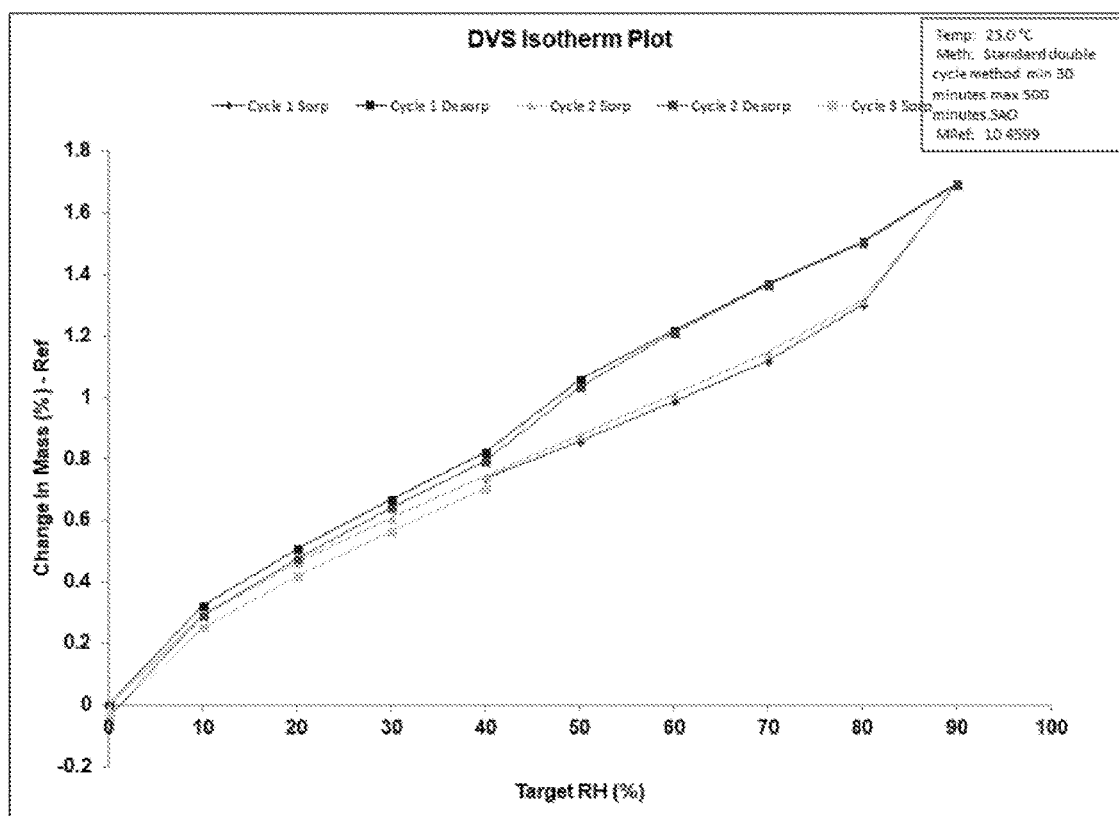
FIG. 11. Illustrates a gravimetric vapor sorption (GVS) analysis of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1), Form 2.
Figure 12:
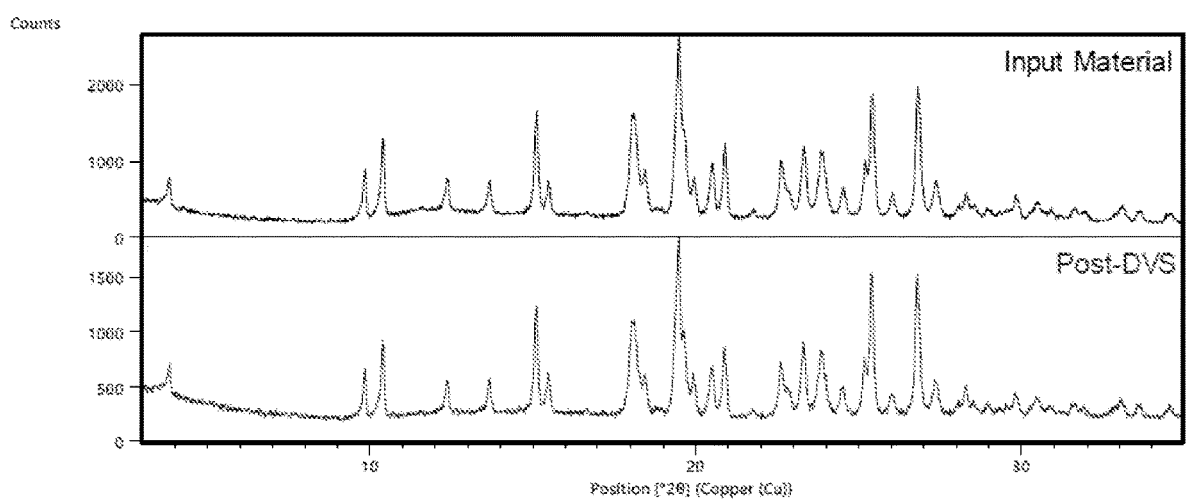
FIG. 12. Illustrates an X-ray powder diffraction (XRPD) pattern of crystalline (R)—N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride (Compound 1) Form 2, pre-GVS and post-GVS.

The DVS analysis of Form 2 of Compound 1 (FIG. 11) showed the material was slightly hygroscopic by DVS with a mass uptake of 1.8% at 90% RH. There was no change in form post-DVS by XRPD (FIG. 12).

III. Polymorph Screen

Amorphous Compound 1 was used for the polymorph screen. Amorphous Compound 1 was prepared in the following manner. A solution of 1.2 g of crystalline Compound 1 in water (150 mL) was equally divided between fifteen 20 mL vials and the vials were frozen at −20° C. The vials were then placed in a desiccator attached to a freeze dryer and dried for about 72 hours. The material was collected and analyzed by XRPD which showed amorphous Compound 1.

Example 7: Solvent Solubility Screen

To amorphous Compound 1 (10 mg) was added 100 μL of the appropriate solvent and if solid remained the vial was gently heated to ~40° C. to aid dissolution. Solvent addition continued until the material fully dissolved or 2 mL had been added (<5 mg/mL). The samples were uncapped and allowed to evaporate at ambient. The solvents used in the solubility screen and results are shown in Table 1.

TABLE 1

| Sample | Solvent | XRPD result |
| --- | --- | --- |
| S-1 | 1,4-Dioxane | Compound 1, Form 1 |
| S-2 | 1-Propanol | Compound 1, Form 1 |
| S-3 | MEK | Compound 1, Form 1/Form 2 |
| S-4 | 40% methanol/60% water | Compound 1, Form 1 |
| S-5 | 95% methanol/5% water | Compound 1, Form 1 |
| S-6 | THF | Compound 1, Form 1 |
| S-7 | Acetone | Compound 1, Form 1 |
| S-8 | Acetonitrile | Compound 1, Form 2 |
| S-9 | Dichloromethane | Compound 1, amorphous |
| S-10 | DMSO | no solid produced |
| S-11 | DMF | no solid produced |
| S-12 | Ethanol | Compound 1, Form 1/Form 2 |
| S-13 | Ethyl acetate | Compound 1, Form 1 |
| S-14 | Methanol | Compound 1, Form 1/Form 2 |
| S-15 | NMP | no solid produced |
| S-16 | 2-Propanol | Compound 1, Form 1 |
| S-17 | Water | no solid produced |

Example 8: Primary Polymorph Screen—Temperature Cycling

Amorphous Compound 1 in ten vials (80 mg) was suspended in the appropriate solvent/solvent mixture and temperature cycled between ambient and 40° C. in 4 hours cycles over 72 hours. The resulting solids were isolated by centrifuge filtration and analyzed by XRPD. The solvents used in the screen and results are shown in Table 2.

TABLE 2

| Solvent | XRPD result |
| --- | --- |
| 1-Propanol | Compound 1, Form 2 |
| MEK | Compound 1, Form 2 |
| 40% methanol/60% water | Compound 1, Form 1 |
| 95% methanol/5% water | Compound 1, Form 1 |
| 2-Propanol | Compound 1, Form 2 |
| Acetonitrile | Compound 1, Form 2 |
| Ethanol | Compound 1, Form 2 |
| Ethyl acetate | Compound 1, amorphous |
| Methanol | Compound 1, Form 2 |
| NMP | insufficient solid produced |
| DMF | Compound 1, Form 2 |
| DMSO | insufficient solid produced |

Example 9: Primary Polymorph Screen—Evaporation

Saturated solutions of Compound 1 were transferred to 2 mL vials. The vials were then uncapped and allowed to evaporate at ambient temperature to recover material. All recovered material was characterised by XRPD. An insufficient volume of saturated solutions was produced during temperature cycling from MEK, 2-propanol, acetonitrile, ethanol, and ethyl acetate. No evaporation experiments were performed in these solvents as a result. Solids were observed from 1-propanol, methanol, NMP and both methanol/water mixtures, but were produced in insufficient quantity, therefore, analysis by XRPD was not conducted.

Example 10: Primary Polymorph Screen—Crash Cool

Saturated solutions of Compound 1 were stored at 2-8° C. for 72 hours. At this time, any material recovered was analysed by XRPD and the vials were moved and stored at −20° C. for 48 hours. After this time, any material recovered was analysed by XRPD. An insufficient volume of saturated solutions was produced during temperature cycling from MEK, 2-propanol, acetonitrile, ethanol, and ethyl acetate. No crash cool experiments were performed in these solvents as a result. Solid was observed after crash cooling at both 2-8° C. and −20° C. from NMP but in both cases, the solid was produced in insufficient quantity, therefore, analysis by XRPD was not conducted.

Example 11: Primary Polymorph Screen—Anti-Solvent Addition

Up to 2 mL of anti-solvent (tBME) was added dropwise to saturated solutions of Compound 1. The samples were left capped, at ambient temperature, for 24 hours, then at 2-8° C. for 24 hours. Any resulting solid was analysed by XRPD. An insufficient volume of saturated solutions was produced during temperature cycling from MEK, 2-propanol, acetonitrile, ethanol, and ethyl acetate. No anti-solvent experiments were performed in these solvents as a result. Solids were observed in anti-solvent experiments in 1-propanol, 95:5 methanol/water, and NMP, but were produced in insufficient quantity, therefore, analysis by XRPD was not conducted. Compound 1, Form 3 was produced in the DMSO anti-solvent experiment.

Example 12: Stability Studies—One Week Study

About 15 mg of Compound 1, Forms 1 and 2 were separately placed at either 40° C./75% RH or 80° C./under ambient light for 1 week. The resulting solids were analysed by XRPD and HPLC purity. No changes in Form 1 or Form 2 were observed under these conditions after 1 week.

Example 13: Stability Studies—Eight Week Study

About 5 mg of Compound 1, Form 1 was weighed into twenty-four, 1.5 mL glass vials. Each vial was placed at either 40° C./75% RH (uncapped vial), 80° C. (capped vial) and under ambient light and temperature (approx. 22° C., capped vial) for a total of 8 weeks. 10 mg was removed from each condition for XRPD, $^1$H NMR and HPLC purity analysis at 1 week, 2 weeks, 4 weeks and 8 weeks. After 8 weeks, XRPD and 41 NMR analysis showed no change. In addition, no significant change in purity was observed by HPLC.

IV. Biological Data

Example 14: RSK2 Inhibition Assay

The RSK2 inhibition assay (in duplicate) was performed at 30° C. for 15 minutes in a final volume of 25 μL according to the following assay reaction recipe:

Component 1: 5 µL of diluted active kinase target (100 ng per reaction)
Component 2: 5 µL of RSK S6K substrate (0.5 µg per reaction)
Component 3: 5 µL of kinase assay buffer
Component 4: 5 µL of Compound 1 (various concentrations: 0, 0.1, 1, 10, 100 or 1000 nM or 1, 3, 10, 30, 100, 300 nM)
Component 5: 5 µL of $^{33}$P-ATP (5 µM stock solution, 0.8 µCi; 20 µM final concentration)

The assay was initiated by the addition of $^{33}$P-ATP and the reaction mixture incubated at 30° C. for 15 minutes. After the incubation period, the assay was terminated by spotting 10 of the reaction mixture onto Multiscreen phosphocellulose P81 plate. The Multiscreen phosphocellulose P81 plate was washed 3 times for approximately 15 minutes each in a 1% phosphoric acid solution. The radioactivity on the P81 plate was counted in the presence of scintillation fluid in a Trilux scintillation counter.

Blank controls were set up for the target kinase which included all the assay components except the addition of the appropriate substrate (which was replaced with equal volume of assay dilution buffer). The corrected activity for each target kinase was determined by removing the blank control value.

Compound 1, when tested in the above-described radioisotope assay, demonstrated the ability to inhibit RSK2. Compound 1: RSK2 $IC_{50}$=18 nM.

We claim:

1. A crystalline form of (R)-N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, wherein the crystalline form of (R)-N-(1-(4-aminobenzyl)-1H-pyrazol-4-yl)-9-methyl-6-oxo-6,7,8,9-tetrahydropyrido[3',2': 4,5]pyrrolo[1,2-a]pyrazine-2-carboxamide hydrochloride is Form 1 having at least one of the following properties:
   (a) an X-ray powder diffraction (XRPD) pattern with characteristic peaks at 9.6° 2-Theta, 16.2° 2-Theta, 18.2° 2-Theta, 21.2° 2-Theta, 22.0° 2-Theta, and 24.8° 2-Theta; and
   (b) a DSC thermogram with a broad endotherm having an onset at about 171° C.

2. The crystalline form of claim 1, wherein the crystalline form has an X-ray powder diffraction (XRPD) pattern with characteristic peaks at 9.6° 2-Theta, 16.2° 2-Theta, 18.2° 2-Theta, 21.2° 2-Theta, 22.0° 2-Theta, and 24.8° 2-Theta.

3. The crystalline form of claim 1, wherein the crystalline form has a DSC thermogram with an endotherm having an onset at about 171° C.

4. The crystalline form of claim 1, wherein the crystalline form is characterized as having properties (a) and (b).

5. A crystalline form of (R)-N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride, wherein the crystalline form of (R)-N-(1-(4-aminobenzyl)-1H-pyrazol-4-yl)-9-methyl-6-oxo-6,7,8,9-tetrahydropyrido[3',2':4,5]pyrrolo[1,2-a]pyrazine-2-carboxamide hydrochloride is Form 2 having at least one of the following properties:
   (a) an X-ray powder diffraction (XRPD) pattern with characteristic peaks at 10.4° 2-Theta, 15.1° 2-Theta, 18.0° 2-Theta, 19.5° 2-Theta, 25.4° 2-Theta, and 26.8° 2-Theta; and
   (b) a DSC thermogram with an endotherm having an onset at about 230° C.

6. The crystalline form of claim 5, wherein the crystalline form has an X-ray powder diffraction (XRPD) pattern with characteristic peaks at 10.4° 2-Theta, 15.1° 2-Theta, 18.0° 2-Theta, 19.5° 2-Theta, 25.4° 2-Theta, and 26.8° 2-Theta.

7. The crystalline form of claim 5, wherein the crystalline form has a DSC thermogram with an endotherm having an onset at about 230° C.

8. The crystalline form of claim 5, wherein the crystalline form is characterized as having properties (a) and (b).

9. A pharmaceutical composition comprising the crystalline form of claim 1, and at least one inactive ingredient selected from pharmaceutically acceptable carriers, diluents, and excipients.

10. A method for treating cancer in an individual in need thereof, comprising administering to the individual a therapeutically effective amount of a crystalline form of claim 1.

11. The method of claim 10, wherein the cancer is breast cancer, prostate cancer, lung cancer, brain cancer, skin cancer, bone cancer, ovarian cancer, multiple myeloma, or leukemia.

12. The method of claim 10, further comprising the administration of a second therapeutic agent.

13. A pharmaceutical composition comprising the crystalline form of claim 5, and at least one inactive ingredient selected from pharmaceutically acceptable carriers, diluents, and excipients.

14. A method for treating cancer in an individual in need thereof, comprising administering to the individual a therapeutically effective amount of a crystalline form of claim 5.

15. The method of claim 14, wherein the cancer is breast cancer, prostate cancer, lung cancer, brain cancer, skin cancer, bone cancer, ovarian cancer, multiple myeloma, or leukemia.

* * * * *